(12) United States Patent
Kinoshita et al.

(10) Patent No.: US 10,374,175 B2
(45) Date of Patent: Aug. 6, 2019

(54) PLATINUM COMPLEX COMPOUND AND ORGANIC ELECTROLUMINESCENCE DEVICE USING THE SAME

(71) Applicant: UDC Ireland, Dublin (IE)

(72) Inventors: Ikuo Kinoshita, Kanagawa (JP); Takeshi Murakami, Kanagawa (JP); Tatsuya Igarashi, Tokyo (JP)

(73) Assignee: UDC IRELAND LIMITED, Dublin (IE)

( * ) Notice: Subject to any disclaimer, the term of this patent is extended or adjusted under 35 U.S.C. 154(b) by 565 days.

(21) Appl. No.: 14/969,162

(22) Filed: Dec. 15, 2015

(65) Prior Publication Data

US 2016/0099426 A1  Apr. 7, 2016

Related U.S. Application Data

(62) Division of application No. 12/333,370, filed on Dec. 12, 2008, now abandoned.

(30) Foreign Application Priority Data

Dec. 14, 2007 (JP) ................. 2007-323682

(51) Int. Cl.
| | |
|---|---|
| H01L 51/54 | (2006.01) |
| C09K 11/06 | (2006.01) |
| H01L 51/00 | (2006.01) |
| C07F 15/00 | (2006.01) |
| C09K 11/02 | (2006.01) |
| H01L 51/50 | (2006.01) |

(52) U.S. Cl.
CPC ...... *H01L 51/0087* (2013.01); *C07F 15/0086* (2013.01); *C09K 11/025* (2013.01); *C09K 11/06* (2013.01); *H01L 51/0072* (2013.01); *C09K 2211/1007* (2013.01); *C09K 2211/1029* (2013.01); *C09K 2211/1044* (2013.01); *C09K 2211/185* (2013.01); *H01L 51/5016* (2013.01)

(58) Field of Classification Search
None
See application file for complete search history.

(56) References Cited

U.S. PATENT DOCUMENTS

| | | | |
|---|---|---|---|
| 7,981,524 B2 | 7/2011 | Ise et al. | |
| 8,247,091 B2 | 8/2012 | Ise et al. | |
| 2005/0170206 A1* | 8/2005 | Ma et al. | ............... C07F 5/069 428/690 |
| 2006/0073359 A1* | 4/2006 | Ise et al. | ............. C07F 15/0086 428/690 |
| 2007/0184301 A1 | 8/2007 | Oshiyama et al. | |

FOREIGN PATENT DOCUMENTS

| | | |
|---|---|---|
| JP | 2007-19462 | 1/2007 |
| WO | 2006/098505 | 9/2006 |

OTHER PUBLICATIONS

Extended European Search Report dated Mar. 12, 2009 for European App. No. 08021623.7.

* cited by examiner

*Primary Examiner* — Marie R. Yamnitzky
(74) *Attorney, Agent, or Firm* — Riverside Law LLP

(57) ABSTRACT

A compound is represented by the following formula (I):

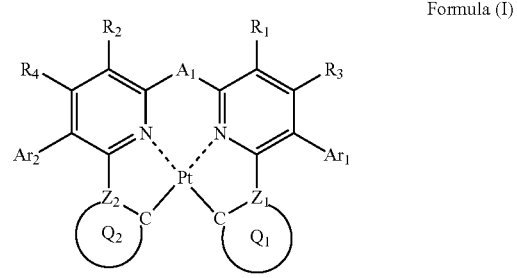

Formula (I)

wherein each of $Ar_1$ and $Ar_2$ independently represents an aromatic ring or an aromatic heterocyclic ring; each of $R_1$, $R_2$, $R_3$ and $R_4$ independently represents a hydrogen atom or a substituent; each of $Z_1$ and $Z_2$ independently represents a carbon atom or a nitrogen atom; each of ring $Q_1$ containing a carbon atom and $Z_1$, and ring $Q_2$ containing a carbon atom and $Z_2$ independently represents an aromatic ring or an aromatic heterocyclic ring; and $A_1$ represents a single bond or a divalent linking group.

13 Claims, No Drawings

PLATINUM COMPLEX COMPOUND AND ORGANIC ELECTROLUMINESCENCE DEVICE USING THE SAME

CROSS-REFERENCE TO RELATED APPLICATION

The present application is a divisional of U.S. patent application Ser. No. 12/333,370, filed on Dec. 12, 2008, which claims priority to Japanese Application No. JP 2007-323682, filed Dec. 14, 2007, all of which applications are incorporated by reference herein in their entireties.

BACKGROUND OF THE INVENTION

1. Field of the Invention

The present invention relates to a platinum complex compound useful as a light-emitting material, and an organic electroluminescence device (hereinafter also referred to as "an organic EL device) using the same.

2. Description of the Related Art

Organic electroluminescent devices are capable of obtaining emission of high luminance by low voltage driving, and actively researched and developed in recent years. An organic EL device generally consists of a pair of electrodes with an organic compound layer including a light-emitting layer, and electrons injected from the cathode and holes injected from the anode are recombined in the light-emitting layer, and generated energy of exciton is used for emission.

The increase in efficiency of the devices has been advanced by the use of phosphorescent materials. Iridium complexes and platinum complexes are known as the phosphorescent materials, and a platinum complex light emitting material capable of light emission of blue to green is reported (e.g., JP-A-2007-19462 (The term "JP-A" as used herein refers to an "unexamined published Japanese patent application".)). The light-emitting layer of an organic electroluminescence device using emission of phosphorescence is formed by the addition of a phosphorescent material to the material bearing charge transportation (a host material).

The improvement of luminance of light emission of an organic electroluminescence device is desired. As a method for improving luminance of light emission of an organic electroluminescence device, a method of increasing addition concentration of the phosphorescent material in a light emitting layer is known. However, by the increase in the addition concentration of a phosphorescent material, light emission of the organic electroluminescence device widens to the long wavelength region, as a result there arises a problem that chromaticity change of light emission becomes large by the addition concentration of the phosphorescent material. Therefore, such a phosphorescent material that chromaticity of emission does not depend upon the addition concentration of the phosphorescent material is desired.

SUMMARY OF THE INVENTION

An object of the invention is to provide an organic electroluminescence device little in chromaticity change due to addition concentration of a phosphorescent material in a light-emitting layer and capable of light emission in higher luminance. Another object is to provide a metal complex compound suitable for the electroluminescence device.

The present inventors have solved the above problems by the invention of the following constitution.

[1] A compound represented by the following formula (I):

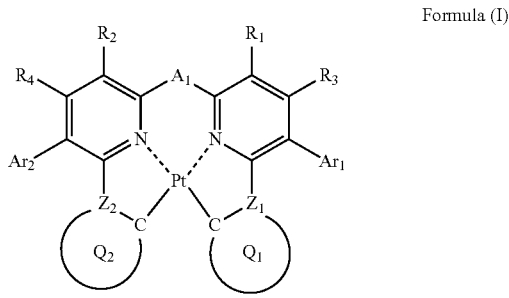

Formula (I)

wherein
each of $Ar_1$ and $Ar_2$ independently represents an aromatic ring or an aromatic heterocyclic ring;
each of $R_1$, $R_2$, $R_3$ and $R_4$ independently represents a hydrogen atom or a substituent;
each of $Z_1$ and $Z_2$ independently represents a carbon atom or a nitrogen atom;
each of ring $Q_1$ containing a carbon atom and $Z_1$, and ring $Q_2$ containing a carbon atom and $Z_2$ independently represents an aromatic ring or an aromatic heterocyclic ring; and
$A_1$ represents a single bond or a divalent linking group.

[2] The compound as described in [1], wherein the formula (I) is represented by the following formula (II):

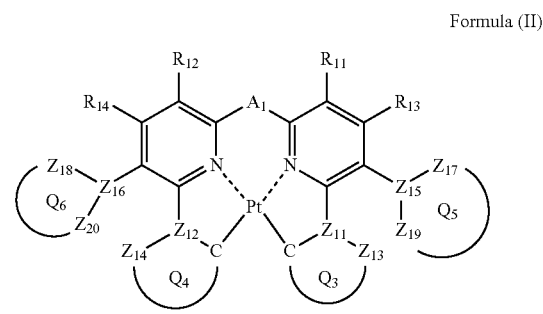

Formula (II)

wherein
each of ring $Q_5$ containing $Z_{15}$, $Z_{17}$ and $Z_{19}$, and ring $Q_6$ containing $Z_{16}$, $Z_{18}$ and $Z_{20}$ independently represents a 5- or 6-membered aromatic ring or aromatic heterocyclic ring;
each of $Z_{15}$, $Z_{16}$, $Z_{17}$, $Z_{18}$, $Z_{19}$ and $Z_{20}$ independently represents a carbon atom or a nitrogen atom;
each of a bond for bonding $Z_{15}$ to $Z_{17}$, a bond for bonding $Z_{15}$ to $Z_{19}$, a bond for bonding $Z_{16}$ to $Z_{18}$, and a bond for bonding $Z_{16}$ to $Z_{20}$ independently represents a single bond or a double bond, provided that when $Z_{15}$ represents a nitrogen atom, each of the bond for bonding $Z_{15}$ to $Z_{17}$ and the bond for bonding $Z_{15}$ to $Z_{19}$ represents a single bond, and when $Z_{16}$ represents a nitrogen atom, each of the bond for bonding $Z_{16}$ to $Z_{18}$ and the bond for bonding $Z_{16}$ to $Z_{20}$ represents a single bond;
$Z_{17}$, $Z_{18}$, $Z_{19}$ and $Z_{20}$ do not have a substituent;
each of ring $Q_3$ containing a carbon atom, $Z_{11}$ and $Z_{13}$, and ring $Q_4$ containing a carbon atom, $Z_{12}$ and $Z_{14}$ independently represents an aromatic ring or an aromatic heterocyclic ring;
each of $Z_{11}$, $Z_{12}$, $Z_{13}$ and $Z_{14}$ independently represents a carbon atom or a nitrogen atom;
each of a bond for bonding $Z_{11}$ to the carbon atom coordinating to Pt contained in ring $Q_3$, a bond for bonding $Z_{11}$ to $Z_{13}$, a bond for bonding $Z_{12}$ to the carbon atom coordinating to Pt contained in ring $Q_4$, and a bond for bonding $Z_{12}$ to $Z_{14}$ independently represents a single bond or a double bond, provided that when $Z_{11}$ represents a nitrogen atom, each of the bond for bonding $Z_{11}$ to the carbon atom coordinating to Pt contained in ring $Q_3$ and the bond for bonding $Z_{11}$ to $Z_{13}$ represents a single bond, and when $Z_{12}$ represents a nitrogen atom, each of the bond for bonding $Z_{12}$ to the carbon atom coordinating to Pt contained in ring $Q_4$ and the bond for bonding $Z_{12}$ to $Z_{14}$ represents a single bond;

$Z_{13}$ and $Z_{14}$ do not have a substituent;

each of $R_{11}$, $R_{12}$, $R_{13}$ and $R_{14}$ independently represents a hydrogen atom or a substituent; and $A_2$ represents a single bond or a divalent linking group.

[3] The compound as described in [2], wherein the formula (II) is represented by the following formula (III):

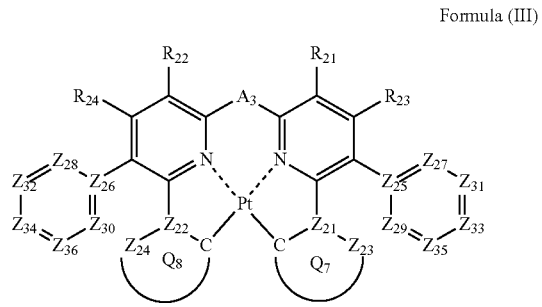

Formula (III)

wherein each of $Z_{25}$ and $Z_{26}$ represents a carbon atom;

each of $Z_{27}$, $Z_{28}$, $Z_{29}$, $Z_{30}$, $Z_{31}$, $Z_{32}$, $Z_{33}$, $Z_{34}$, $Z_{35}$ and $Z_{36}$ independently represents a carbon atom or a nitrogen atom;

$Z_{27}$, $Z_{28}$, $Z_{29}$ and $Z_{30}$ do not have a substituent;

each of $Z_{21}$, $Z_{22}$, $Z_{23}$ and $Z_{24}$ independently represents a carbon atom or a nitrogen atom;

each of ring $Q_7$ containing a carbon atom, $Z_{21}$ and $Z_{23}$ and ring $Q_8$ containing a carbon atom, $Z_{22}$ and $Z_{24}$ independently represents an aromatic ring or an aromatic heterocyclic ring;

each of a bond for bonding $Z_{21}$ to the carbon atom coordinating to Pt contained in ring $Q_7$, a bond for bonding $Z_{21}$ to $Z_{23}$, a bond for bonding $Z_{22}$ to the carbon atom coordinating to Pt contained in ring $Q_8$, and a bond for bonding $Z_{22}$ to $Z_{24}$ independently represents a single bond or a double bond, provided that when $Z_{21}$ represents a nitrogen atom, each of the bond for bonding $Z_{21}$ to the carbon atom coordinating to Pt contained in ring $Q_7$ and the bond for bonding $Z_{21}$ to $Z_{23}$ represents a single bond, and when $Z_{22}$ represents a nitrogen atom, each of the bond for bonding $Z_{22}$ to the carbon atom coordinating to Pt contained in ring $Q_8$ and the bond for bonding $Z_{22}$ to $Z_{24}$ represents a single bond;

$Z_{23}$ and $Z_{24}$ do not have a substituent;

each of $R_{21}$, $R_{22}$, $R_{23}$ and $R_{24}$ independently represents a hydrogen atom or a substituent; and $A_3$ represents a single bond or a divalent linking group.

[4] The compound as described in [3], wherein the formula (III) is represented by the following formula (IV):

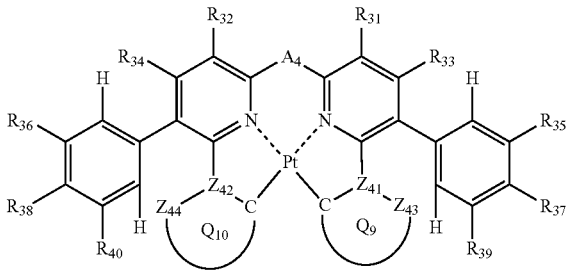

Formula (IV)

wherein each of $Z_{41}$, $Z_{42}$, $Z_{43}$ and $Z_{44}$ independently represents a carbon atom or a nitrogen atom;

each of ring $Q_9$ containing a carbon atom, $Z_{41}$ and $Z_{43}$ and ring $Q_{10}$ containing a carbon atom, $Z_{42}$ and $Z_{44}$ independently represents an aromatic ring or an aromatic heterocyclic ring;

each of a bond for bonding $Z_{41}$ to the carbon atom coordinating to Pt contained in ring $Q_9$, a bond for bonding $Z_{41}$ to $Z_{43}$, a bond for bonding $Z_{42}$ to the carbon atom coordinating to Pt contained in ring $Q_{10}$, and a bond for bonding $Z_{42}$ to $Z_{44}$ independently represents a single bond or a double bond, provided that when $Z_{41}$ represents a nitrogen atom, each of the bond for bonding $Z_{41}$ to the carbon atom coordinating to Pt contained in ring $Q_9$ and the bond for bonding $Z_{41}$ to $Z_{43}$ represents a single bond, and when $Z_{42}$ represents a nitrogen atom, each of the bond for bonding $Z_{42}$ to the carbon atom coordinating to Pt contained in ring $Q_{10}$ and the bond for bonding $Z_{42}$ to $Z_{44}$ represents a single bond;

$Z_{43}$ and $Z_{44}$ do not have a substituent;

each of $R_{31}$, $R_{32}$, $R_{33}$, $R_{34}$, $R_{35}$, $R_{36}$, $R_{37}$, $R_{38}$, $R_{39}$ and $R_{40}$ independently represents a hydrogen atom or a substituent; and $A_4$ represents a single bond or a divalent linking group.

[5] The compound as described in [4], wherein the formula (IV) is represented by the following formula (V):

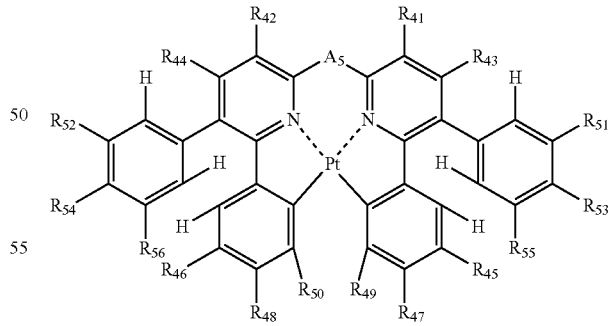

Formula (V)

wherein each of $R_{41}$, $R_{42}$, $R_{43}$, $R_{44}$, $R_{45}$, $R_{46}$, $R_{47}$, $R_{48}$, $R_{49}$, $R_{50}$, $R_{51}$, $R_{52}$, $R_{53}$, $R_{54}$, $R_{55}$ and $R_{56}$ independently represents a hydrogen atom or a substituent; and $A_5$ represents a single bond or a divalent linking group.

[6] The compound as described in [4], wherein the formula (IV) is represented by the following formula (VI):

Formula (VI)

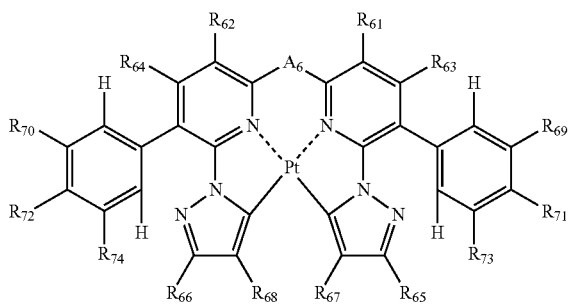

wherein
each of $R_{61}$, $R_{62}$, $R_{63}$, $R_{64}$, $R_{65}$, $R_{66}$, $R_{67}$, $R_{68}$, $R_{69}$, $R_{70}$, $R_{71}$, $R_{72}$, $R_{73}$ and $R_{74}$ independently represents a hydrogen atom or a substituent; and $A_6$ represents a single bond or a divalent linking group.

The compound as described in [2], wherein the formula (II) is represented by the following formula (VII):

Formula (VII)

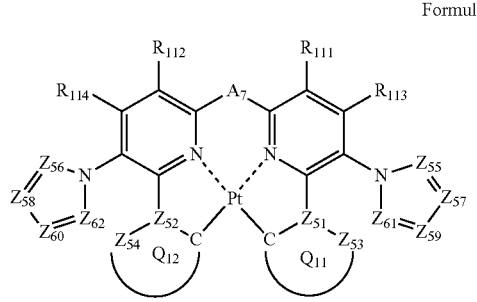

wherein
each of $Z_{55}$, $Z_{56}$, $Z_{57}$, $Z_{58}$, $Z_{59}$, $Z_{60}$, $Z_{61}$ and $Z_{62}$ independently represents a carbon atom or a nitrogen atom;

$Z_{55}$, $Z_{56}$, $Z_{61}$ and $Z_{62}$ do not have a substituent;

each of $Z_{51}$, $Z_{52}$, $Z_{53}$ and $Z_{54}$ independently represents a carbon atom or a nitrogen atom, each of ring $Q_{11}$ containing a carbon atom, $Z_{51}$ and $Z_{53}$ and ring $Q_{12}$ containing a carbon atom, $Z_{52}$ and $Z_{54}$ independently represents an aromatic ring or an aromatic heterocyclic ring, each of a bond for bonding $Z_{51}$ to the carbon atom coordinating to Pt contained in ring $Q_{11}$, a bond for bonding $Z_{51}$ to $Z_{53}$, a bond for bonding $Z_{52}$ to the carbon atom coordinating to Pt contained in ring $Q_{12}$, and a bond for bonding $Z_{52}$ to $Z_{54}$ independently represents a single bond or a double bond, provided that when $Z_{51}$ represents a nitrogen atom, each of the bond for bonding $Z_{51}$ to the carbon atom coordinating to Pt contained in ring $Q_{11}$ and the bond for bonding $Z_{51}$ to $Z_{53}$ represents a single bond, and when $Z_{52}$ represents a nitrogen atom, each of the bond for bonding $Z_{52}$ to the carbon atom coordinating to Pt contained in ring $Q_{12}$ and the bond for bonding $Z_{52}$ to $Z_{54}$ represents a single bond; and $Z_{53}$ and $Z_{54}$ do not have a substituent;

each of $R_{111}$, $R_{112}$, $R_{113}$ and $R_{114}$ independently represents a hydrogen atom or a substituent; and $A_7$ represents a single bond or a divalent linking group.

[8] The compound as described in [7], wherein the formula (VII) is represented by the following formula (VIII):

Formula (VIII)

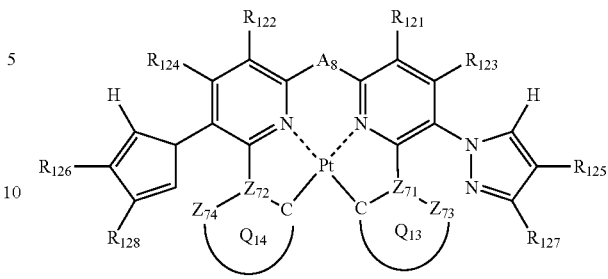

wherein
each of $Z_{71}$, $Z_{72}$, $Z_{73}$ and $Z_{74}$ independently represents a carbon atom or a nitrogen atom;

each of ring $Q_{13}$ containing a carbon atom, $Z_{71}$ and $Z_{73}$ and ring $Q_{14}$ containing a carbon atom, $Z_{72}$ and $Z_{74}$ independently represents an aromatic ring or an aromatic heterocyclic ring;

each of a bond for bonding $Z_{71}$ to the carbon atom coordinating to Pt contained in ring $Q_{13}$, a bond for bonding $Z_{71}$ to $Z_{73}$, a bond for bonding $Z_{72}$ to the carbon atom coordinating to Pt contained in ring $Q_{14}$, and a bond for bonding $Z_{72}$ to $Z_{74}$ independently represents a single bond or a double bond, provided that when $Z_{71}$ represents a nitrogen atom, each of the bond for bonding $Z_{71}$ to the carbon atom coordinating to Pt contained in ring $Q_{13}$ and the bond for bonding $Z_{71}$ to $Z_{73}$ represents a single bond, and when $Z_{72}$ represents a nitrogen atom, each of the bond for bonding $Z_{72}$ to the carbon atom coordinating to Pt contained in ring $Q_{14}$ and the bond for bonding $Z_{72}$ to $Z_{74}$ represents a single bond;

$Z_{73}$ and $Z_{74}$ do not have a substituent;

each of $R_{121}$, $R_{122}$, $R_{123}$, $R_{124}$, $R_{125}$, $R_{126}$, $R_{127}$ and $R_{128}$ independently represents a hydrogen atom or a substituent; and $A_8$ represents a single bond or a divalent linking group.

[9] The compound as described in [8], wherein
the formula (VIII) is represented by the following formula (IX):

Formula (IX)

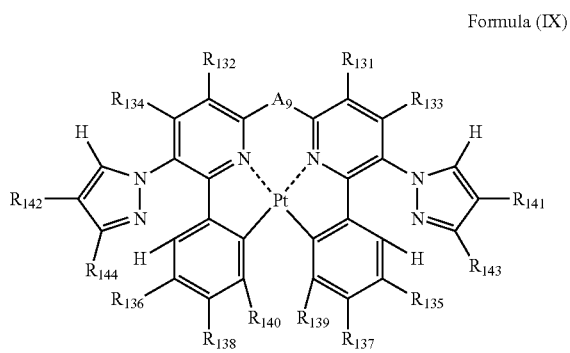

wherein
each of $R_{131}$, $R_{132}$, $R_{133}$, $R_{134}$, $R_{135}$, $R_{136}$, $R_{137}$, $R_{138}$, $R_{139}$, $R_{140}$, $R_{141}$, $R_{142}$, $R_{143}$ and $R_{144}$ independently represents a hydrogen atom or a substituent; and $A_9$ represents a single bond or a divalent linking group.

[10] The compound as described in [8], wherein
the formula (VIII) is represented by the following formula (X):

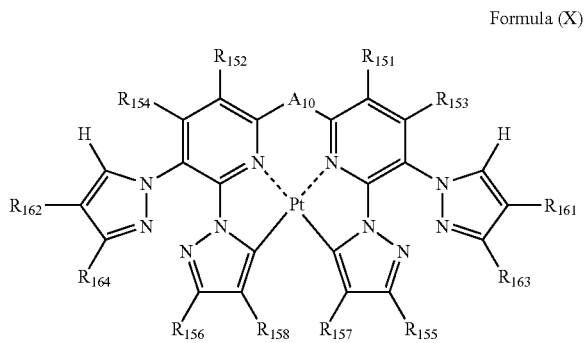

Formula (X)

wherein each of $R_{151}$, $R_{152}$, $R_{153}$, $R_{154}$, $R_{155}$, $R_{156}$, $R_{157}$, $R_{158}$, $R_{161}$, $R_{162}$, $R_{163}$ and $R_{164}$ independently represents a hydrogen atom or a substituent; and $A_{10}$ represents a single bond or a divalent linking group.

[11] An organic electroluminescence device comprising:
a pair of electrodes; and
an organic layer between the pair of electrodes,
wherein the organic layer contains the compound as described in [1].

[12] An organic electroluminescence device comprising:
a pair of electrodes; and
a light-emitting layer between the pair of electrodes,
wherein the light-emitting layer contains the compound as described in [1] in a proportion of from 20 to 30 wt % of the total mass of the light-emitting layer.

DETAILED DESCRIPTION OF THE INVENTION

Substituent group B is defined as follows in the invention.
Substituent Group B:

An alkyl group (preferably having from 1 to 30 carbon atoms, more preferably from 1 to 20 carbon atoms, and especially preferably from 1 to 10 carbon atoms, e.g., methyl, ethyl, isopropyl, tert-butyl, n-octyl, n-decyl, n-hexadecyl, cyclopropyl, cyclopentyl, cyclohexyl, etc., are exemplified), an alkenyl group (preferably having from 2 to 30 carbon atoms, more preferably from 2 to 20 carbon atoms, and especially preferably from 2 to 10 carbon atoms, e.g., vinyl, allyl, 2-butenyl, 3-pentenyl, etc., are exemplified), an alkynyl group (preferably having from 2 to 30 carbon atoms, more preferably from 2 to 20 carbon atoms, and especially preferably from 2 to 10 carbon atoms, e.g., propargyl, 3-pentynyl, etc., are exemplified), an aryl group (preferably having from 6 to 30 carbon atoms, more preferably from 6 to 20 carbon atoms, and especially preferably from 6 to 12 carbon atoms, e.g., phenyl, p-methylphenyl, naphthyl, anthranyl, etc., are exemplified), an amino group (preferably having from 0 to 30 carbon atoms, more preferably from 0 to 20 carbon atoms, and especially preferably from 0 to 10 carbon atoms, e.g., amino, methylamino, dimethylamino, diethylamino, dibenzylamino, diphenylamino, ditolylamino, etc., are exemplified), an alkoxyl group (preferably having from 1 to 30 carbon atoms, more preferably from 1 to 20 carbon atoms, and especially preferably from 1 to 10 carbon atoms, e.g., methoxy, ethoxy, butoxy, 2-ethylhexyloxy, etc., are exemplified), an aryloxy group (preferably having from 6 to 30 carbon atoms, more preferably from 6 to 20 carbon atoms, and especially preferably from 6 to 12 carbon atoms, e.g., phenyloxy, 1-naphthyloxy, 2-naphthyloxy, etc., are exemplified), a heterocyclic oxy group (preferably having from 1 to 30 carbon atoms, more preferably from 1 to 20 carbon atoms, and especially preferably from 1 to 12 carbon atoms, e.g., pyridyloxy, pyrazyloxy, pyrimidyloxy, quinolyloxy, etc., are exemplified), an acyl group (preferably having from 1 to 30 carbon atoms, more preferably from 1 to 20 carbon atoms, and especially preferably from 1 to 12 carbon atoms, e.g., acetyl, benzoyl, formyl, pivaloyl, etc., are exemplified), an alkoxycarbonyl group (preferably having from 2 to 30 carbon atoms, more preferably from 2 to 20 carbon atoms, and especially preferably from 2 to 12 carbon atoms, e.g., methoxycarbonyl, ethoxycarbonyl, etc., are exemplified), an aryloxycarbonyl group (preferably having from 7 to 30 carbon atoms, more preferably from 7 to 20 carbon atoms, and especially preferably from 7 to 12 carbon atoms, e.g., phenyloxycarbonyl, etc., are exemplified), an acyloxy group (preferably having from 2 to 30 carbon atoms, more preferably from 2 to 20 carbon atoms, and especially preferably from 2 to 10 carbon atoms, e.g., acetoxy, benzoyloxy, etc., are exemplified), an acylamino group (preferably having from 2 to 30 carbon atoms, more preferably from 2 to 20 carbon atoms, and especially preferably from 2 to 10 carbon atoms, e.g., acetylamino, benzoylamino, etc., are exemplified), an alkoxycarbonylamino group (preferably having from 2 to 30 carbon atoms, more preferably from 2 to 20 carbon atoms, and especially preferably from 2 to 12 carbon atoms, e.g., methoxycarbonylamino, etc., are exemplified), an aryloxycarbonylamino group (preferably having from 7 to 30 carbon atoms, more preferably from 7 to 20 carbon atoms, and especially preferably from 7 to 12 carbon atoms, e.g., phenyloxycarbonylamino, etc., are exemplified), a sulfonylamino group (preferably having from 1 to 30 carbon atoms, more preferably from 1 to 20 carbon atoms, and especially preferably from 1 to 12 carbon atoms, e.g., methanesulfonylamino, benzenesulfonylamino, etc., are exemplified), a sulfamoyl group (preferably having from 0 to 30 carbon atoms, more preferably from 0 to 20 carbon atoms, and especially preferably from 0 to 12 carbon atoms, e.g., sulfamoyl, methylsulfamoyl, dimethylsulfamoyl, phenylsulfamoyl, etc., are exemplified), a carbamoyl group (preferably having from 1 to 30 carbon atoms, more preferably from 1 to 20 carbon atoms, and especially preferably from 1 to 12 carbon atoms, e.g., carbamoyl, methylcarbamoyl, diethylcarbamoyl, phenylcarbamoyl, etc., are exemplified), an alkylthio group (preferably having from 1 to 30 carbon atoms, more preferably from 1 to 20 carbon atoms, and especially preferably from 1 to 12 carbon atoms, e.g., methylthio, ethylthio, etc., are exemplified), an arylthio group (preferably having from 6 to 30 carbon atoms, more preferably from 6 to 20 carbon atoms, and especially preferably from 6 to 12 carbon atoms, e.g., phenylthio, etc., are exemplified), a heterocyclic thio group (preferably having from 1 to 30 carbon atoms, more preferably from 1 to 20 carbon atoms, and especially preferably from 1 to 12 carbon atoms, e.g., pyridylthio, 2-benzimizolylthio, 2-benzoxazolylthio, 2-benzothiazolylthio, etc., are exemplified), a sulfonyl group (preferably having from 1 to 30 carbon atoms, more preferably from 1 to 20 carbon atoms, and especially preferably from 1 to 12 carbon atoms, e.g., mesyl, tosyl, etc., are exemplified), a sulfinyl group (preferably having from 1 to 30 carbon atoms, more preferably from 1 to 20 carbon atoms, and especially preferably from 1 to 12 carbon atoms, e.g., methanesulfinyl, benzenesulfinyl, etc., are exemplified), a ureido group (preferably having from 1 to 30 carbon atoms, more preferably from 1 to 20 carbon atoms, and especially preferably from 1 to 12 carbon atoms, e.g., ureido, methylureido, phenylureido, etc., are exemplified), a phosphoric acid amido group (preferably having from 1 to 30 carbon atoms, more preferably from 1 to 20 carbon atoms, and especially preferably from 1 to 12 carbon atoms, e.g., diethylphosphoric acid amido, phenylphosphoric acid amido, etc., are exemplified), a hydroxyl group, a mercapto group, a halogen atom (e.g., a fluorine atom, a chlorine atom, a bromine atom, an iodine atom), a cyano group, a sulfo group, a carboxyl group, a nitro group, a hydroxamic acid group, a sulfino group, a hydrazino group, an imino group, a heterocyclic (heteroaryl) group (preferably having from 1 to 30 carbon atoms, and more preferably from 1 to 12 carbon atoms, and as the hetero atoms, e.g., a nitrogen atom, an oxygen atom, and a sulfur atom are exemplified, specifically, e.g., imidazolyl, pyridyl, quinolyl, furyl, thienyl, piperidyl, morpholino, benzoxazolyl, benzimidazolyl, benzothiazolyl, a carbazolyl group, an azepinyl group, etc., are exemplified), a silyl group (preferably having from 3 to 40 carbon atoms, more preferably from 3 to 30 carbon atoms, and especially preferably from 3 to 24 carbon atoms, e.g., trimethylsilyl, triphenylsilyl, etc., are exemplified), a silyloxy group (preferably having from 3 to 40 carbon atoms, more preferably from 3 to 30 carbon atoms, and especially preferably from 3 to 24 carbon atoms, e.g., trimethylsilyloxy, triphenylsilyloxy, etc., are exemplified), a phosphoryl group (e.g., a diphenylphosphoryl group, a dimethylphosphoryl group, etc., are exemplified), etc., are exemplified. These substituents may further be substituted, and the substituents selected from substituent group B described above can be exemplified as further substituents.

The compound in the invention is represented by the following formula (I).

A platinum complex having a tetradentate ligand represented by formula (I) (hereinafter sometimes referred to as "the complex in the invention" or "the platinum complex") will be described below.

The hydrogen atoms in the following explanation of formulae (I), (II), (III), (IV), (V), (VI), (VII), (VIII), (IX) and (X) also include the isotopes (e.g., deuterium atoms, etc.), and atoms further having a substituent mean to contain the isotopes thereof.

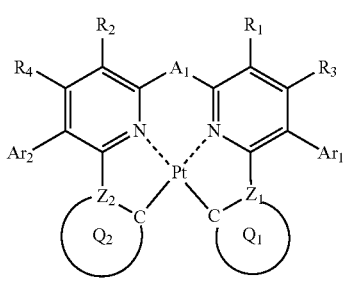

Formula (I)

In formula (I), each of $Ar_1$ and $Ar_2$ independently represents an aromatic ring or an aromatic heterocyclic ring; each of $R_1$, $R_2$, $R_3$ and $R_4$ independently represents a hydrogen atom or a substituent; each of $Z_1$ and $Z_2$ independently represents a carbon atom or a nitrogen atom, and each of ring $Q_1$ containing a carbon atom and $Z_1$, and ring $Q_2$ containing a carbon atom and $Z_2$ independently represents an aromatic ring or an aromatic heterocyclic ring; and $A_1$ represents a single bond or a divalent linking group.

As $Ar_1$ and $Ar_2$, a ring little in reaction activity is preferred for the purpose of increasing stability of the platinum complex, and to lessen change of emission wavelength of the platinum complex by substitution, a ring small in broadening of π conjugation is preferred. A benzene ring, a pyridine ring, a pyrazine ring, a pyrimidine ring, a pyridazine ring, a pyrrole ring, a thiophene ring, a furan ring, a pyrazole ring, an imidazole ring, a triazole ring, an oxazole ring, and a thiazole ring are preferred, more preferably a benzene ring, a pyridine ring, a pyrazine ring, a pyrrole ring, a thiophene ring, a pyrazole ring, and an imidazole ring are exemplified, still more preferably a benzene ring, a pyridine ring, and a pyrazole ring, and most preferably a benzene ring.

As the examples of the substituents represented by $R_1$, $R_2$, $R_3$ and $R_4$, the substituents selected from substituent group B can be exemplified. As the substituents represented by $R_1$, $R_2$, $R_3$ and $R_4$, a hydrogen atom, an alkyl group, an aryl group, an amino group, an alkoxyl group, an aryloxy group, an acyl group, an alkoxycarbonyl group, an alkylthio group, a sulfonyl group, a hydroxyl group, a halogen atom, a cyano group, a nitro group, and a heterocyclic group are preferred, a hydrogen atom, an alkyl group, an aryl group, a halogen atom, a cyano group, and a heterocyclic group are more preferred, a hydrogen atom, a methyl group, a t-butyl group, a trifluoromethyl group, a phenyl group, a fluorine atom, a cyano group, and a pyridyl group are still more preferred, a hydrogen atom, a methyl group, and a fluorine atom are still further preferred, and a hydrogen atom is especially preferred. $R_1$, $R_2$, $R_3$ and $R_4$ may be bonded to each other to form a ring, if possible.

In order for a platinum complex to emit light in the visible region, ring $Q_1$ and ring $Q_2$ are preferably a 5-membered ring, a 6-membered ring, a condensed ring of a 5-membered ring and a 6-membered ring, a condensed ring of a 6-membered ring and a 6-membered ring, and a condensed ring of a 6-membered ring, a 6-membered ring, and a 6-membered ring, and to emit light in the blue to green regions, a 5-membered ring and a 6-membered ring are more preferred. As ring $Q_1$ and ring $Q_2$, preferably a benzene ring, a naphthalene ring, an anthracene ring, a pyridine ring, a pyrazine ring, a pyrimidine ring, a pyridazine ring, a quinoline ring, a pyrrole ring, a thiophene ring, a furan ring, a pyrazole ring, an imidazole ring, a triazole ring, an oxazole ring, a thiazole ring, an indole ring, a benzopyrazole ring, or a benzimidazole ring, more preferably a benzene ring, a pyridine ring, a pyrazine ring, a pyrrole ring, a pyrazole ring, or an imidazole ring, still more preferably a benzene ring, a pyridine ring, or a pyrazole ring, and most preferably a benzene ring or a pyrazole ring.

$A_1$ represents a single bond or a divalent linking group. As the examples of the divalent linking groups represented by $A_1$, an alkylene group (e.g., methylene, ethylene, propylene, etc.), an arylene group (e.g., phenylene, naphthalenediyl), a heteroarylene group (e.g., pyridinediyl, thiophenediyl, etc.), an imino group (—NR—) (e.g., a phenylimino group, etc.), an oxy group (—O—), a thio group (—S—), a phosphinidene group (—PR—) (e.g., a phenylphosphinidene group, etc.), a silylene group (—SiRR'—) (e.g., a dimethylsilylene group, a diphenylsilylene group, etc.), and combination of these groups are exemplified. These linking groups may further have a substituent.

$A_1$ preferably represents a single bond, an alkylene group, an arylene group, a heteroarylene group, an imino group, an oxy group, a thio group, or a silylene group, more preferably a single bond, an alkylene group, an arylene group, or an imino group, still more preferably a single bond, a methylene group, a phenylene group, or a nitrogen atom having a phenyl group, still yet further preferably a single bond, or a di-substituted methylene group, still yet more preferably a single bond, a dimethylmethylene group, a diethylmethylene group, a diisobutylmethylene group, a dibenzylmethylene group, an ethylmethylmethylene group, a methylpropylmethylene group, an isobutylmethylmethylene group, a diphenylmethylene group, a methylphenylmethylene group, a cyclohexanediyl group, a cyclopentanediyl group, a fluorenediyl group, or a fluoromethylmethylene group, and especially preferably a single bond, a dimethylmethylene group, a diphenylmethylene group, or a cyclohexanediyl group. The specific examples of the divalent linking groups are shown below, but the invention is not restricted thereto.

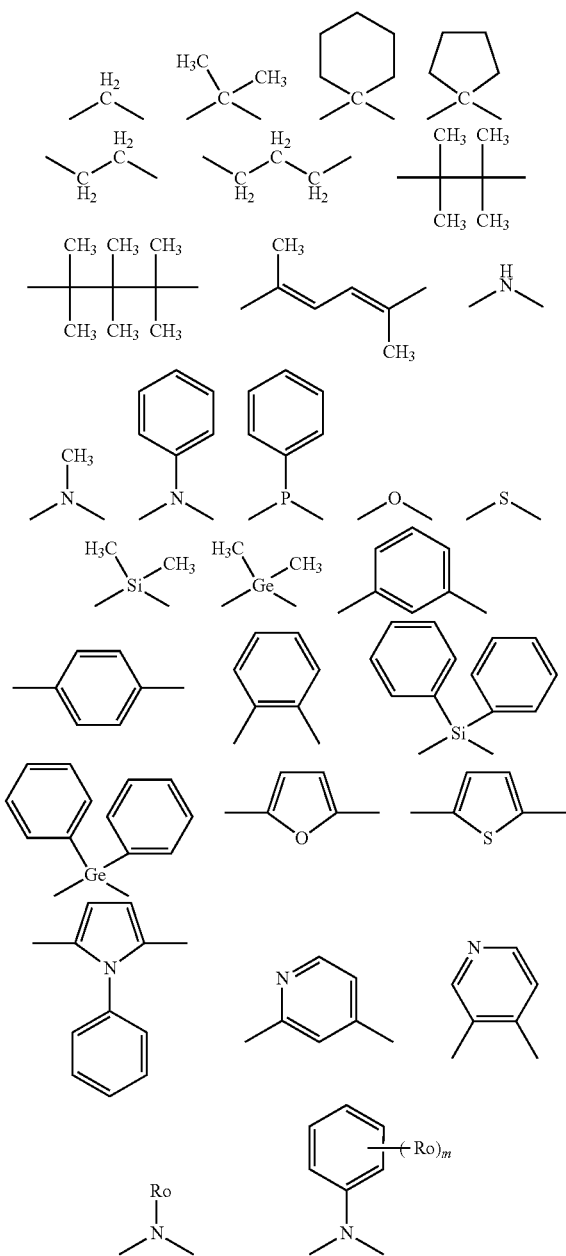

In the above formulae, $R_0$ represents a substituent selected from substituent group B. $R_0$ is preferably an alkyl group, and more preferably an alkyl group having from 1 to 6 carbon atoms. m represents an integer of from 1 to 5. m is preferably from 2 to 5, and more preferably 2 or 3.

The relationships of formulae in the invention are as follows.

Formula (I) is preferably represented by formula (II).
Formula (II) is preferably represented by formula (III) or (VII).
Formula (III) is preferably represented by formula (IV).
Formula (IV) is preferably represented by formula (V) or (VI).
Formula (VII) is preferably represented by formula (VIII).
Formula (VIII) is preferably represented by formula (IX) or (X).
Formula (II) will be described below.

Formula (II)

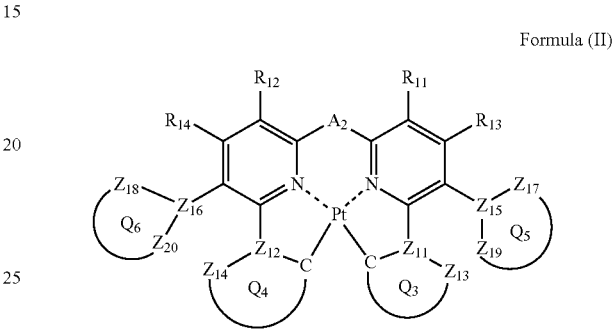

In formula (II), each of ring $Q_5$ containing $Z_{15}$, $Z_{17}$ and $Z_{19}$, and ring $Q_6$ containing $Z_{16}$, $Z_{18}$ and $Z_{20}$ independently represents a 5- or 6-membered aromatic ring or an aromatic heterocyclic ring; each of $Z_{15}$, $Z_{16}$, $Z_{17}$, $Z_{18}$, $Z_{19}$ and $Z_{20}$ independently represents a carbon atom or a nitrogen atom, and each of a bond for bonding $Z_{15}$ to $Z_{17}$, a bond for bonding $Z_{15}$ to $Z_{19}$, a bond for bonding $Z_{16}$ to $Z_{18}$, and a bond for bonding $Z_{16}$ to $_{20}$ independently represents a single bond or a double bond, provided that when $Z_{15}$ represents a nitrogen atom, each of the bond for bonding $Z_{15}$ to $Z_{17}$ and the bond for bonding $Z_{15}$ to $Z_{19}$ represents a single bond, and when $Z_{16}$ represents a nitrogen atom, each of the bond for bonding $Z_{16}$ to $Z_{18}$ and the bond for bonding $Z_{16}$ to $Z_{20}$ represents a single bond, and $Z_{17}$, $Z_{18}$, $Z_{19}$ and $Z_{20}$ do not have a substituent; each of ring $Q_3$ containing a carbon atom, $Z_{11}$ and $Z_{13}$, and ring $Q_4$ containing a carbon atom, $Z_{12}$ and $Z_{14}$ independently represents an aromatic ring or an aromatic heterocyclic ring, each of $Z_{11}$, $Z_{12}$, $Z_{13}$ and $Z_{14}$ independently represents a carbon atom or a nitrogen atom, each of a bond for bonding $Z_{11}$ to the carbon atom coordinating to Pt contained in ring $Q_3$, a bond for bonding $Z_{11}$ to $Z_{13}$, a bond for bonding $Z_{12}$ to the carbon atom coordinating to Pt contained in ring $Q_4$, and a bond for bonding $Z_{12}$ to $Z_{14}$ independently represents a single bond or a double bond, provided that when $Z_{11}$ represents a nitrogen atom, each of the bond for bonding $Z_{11}$ to the carbon atom coordinating to Pt contained in ring $Q_3$ and the bond for bonding $Z_{11}$ to $Z_{13}$ represents a single bond, and when $Z_{12}$ represents a nitrogen atom, each of the bond for bonding $Z_{12}$ to the carbon atom coordinating to Pt contained in ring $Q_4$ and the bond for bonding $Z_{12}$ to $Z_{14}$ represents a single bond, and $Z_{13}$ and $Z_{14}$ do not have a substituent; each of $R_{11}$, $R_{12}$, $R_{13}$ and $R_{14}$ independently represents a hydrogen atom or a substituent; and $A_2$ represents a single bond or a divalent linking group.

Each of ring $Q_5$ and ring $Q_6$ independently represents an aromatic ring or an aromatic heterocyclic ring. As ring $Q_5$ and ring $Q_6$, a ring little in reaction activity is preferred for the purpose of increasing stability of the platinum complex, and to lessen change of emission wavelength of the platinum complex by substitution, a ring small in broadening of π conjugation is preferred. A benzene ring, a pyridine ring, a pyrazine ring, a pyrimidine ring, a pyridazine ring, a pyrrole ring, a thiophene ring, a furan ring, a pyrazole ring, an imidazole ring, a triazole ring, an oxazole ring, and a thiazole ring are preferred, more preferably a benzene ring, a pyridine ring, a pyrazine ring, a pyrrole ring, a thiophene ring, a pyrazole ring, and an imidazole ring are exemplified, still more preferably a benzene ring, a pyridine ring, and a pyrazole ring, and most preferably a benzene ring.

Each of $R_{11}$, $R_{12}$, $R_{13}$ and $R_{14}$ has the same meaning as that of $R_1$, $R_2$, $R_3$ and $R_4$ in formula (I), and the preferred range is also the same.

In order for a platinum complex to emit light in the visible region, ring $Q_3$ and ring $Q_4$ are preferably a 5-membered ring, a 6-membered ring, a condensed ring of a 5-membered ring and a 6-membered ring, a condensed ring of a 6-membered ring and a 6-membered ring, and a condensed ring of a 6-membered ring, a 6-membered ring, and a 6-membered ring, and to emit light in the blue to green regions, a 5-membered ring and a 6-membered ring are more preferred. As ring $Q_3$ and ring $Q_4$, preferably a benzene ring, a naphthalene ring, an anthracene ring, a pyridine ring, a pyrazine ring, a pyrimidine ring, a pyridazine ring, a quinoline ring, a pyrrole ring, a thiophene ring, a furan ring, a pyrazole ring, an imidazole ring, a triazole ring, an oxazole ring, a thiazole ring, an indole ring, a benzopyrazole ring, or a benzimidazole ring, more preferably a benzene ring, a pyridine ring, a pyrazine ring, a pyrrole ring, a pyrazole ring, or an imidazole ring, still more preferably a benzene ring, a pyridine ring, or a pyrazole ring, and most preferably a benzene ring or a pyrazole ring.

$A_2$ has the same meaning as that of $A_1$ in formula (I), and the preferred range is also the same.

Formula (III) will be described below.

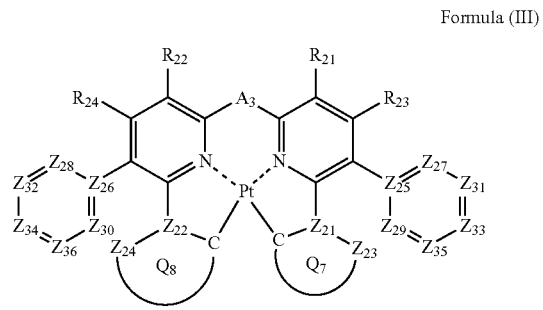

Formula (III)

In formula (III), each of $Z_{25}$ and $Z_{26}$ represents a carbon atom; each of $Z_{27}$, $Z_{28}$, $Z_{29}$, $Z_{30}$, $Z_{31}$, $Z_{32}$, $Z_{33}$, $Z_{34}$, $Z_{35}$ and $Z_{36}$ independently represents a carbon atom or a nitrogen atom, and $Z_{27}$, $Z_{28}$, $Z_{29}$ and $Z_{30}$ do not have a substituent; each of $Z_{21}$, $Z_{22}$, $Z_{23}$ and $Z_{24}$ independently represents a carbon atom or a nitrogen atom, each of ring $Q_7$ containing a carbon atom, $Z_{21}$ and $Z_{23}$ and ring $Q_8$ containing a carbon atom, $Z_{22}$ and $Z_{24}$ independently represents an aromatic ring or an aromatic heterocyclic ring, each of a bond for bonding $Z_{21}$ to the carbon atom coordinating to Pt contained in ring $Q_7$, a bond for bonding $Z_{21}$ to $Z_{23}$, a bond for bonding $Z_{22}$ to the carbon atom coordinating to Pt contained in ring $Q_8$, and a bond for bonding $Z_{22}$ to $Z_{24}$ independently represents a single bond or a double bond, provided that when $Z_{21}$ represents a nitrogen atom, each of the bond for bonding $Z_{21}$ to the carbon atom coordinating to Pt contained in ring $Q_7$ and the bond for bonding $Z_{21}$ to $Z_{23}$ represents a single bond, and when $Z_{22}$ represents a nitrogen atom, each of the bond for bonding $Z_{22}$ to the carbon atom coordinating to Pt contained in ring $Q_8$ and the bond for bonding $Z_{22}$ to $Z_{24}$ represents a single bond, and $Z_{23}$ and $Z_{24}$ do not have a substituent; each of $R_{21}$, $R_{22}$, $R_{23}$ and $R_{24}$ independently represents a hydrogen atom or a substituent; and $A_3$ represents a single bond or a divalent linking group.

Each of $Z_{25}$, $Z_{27}$, $Z_{29}$, $Z_{31}$, $Z_{33}$ and $Z_{35}$, and $Z_{26}$, $Z_{28}$, $Z_{30}$, $Z_{32}$, $Z_{34}$ and $Z_{36}$ independently forms an aromatic ring or an aromatic heterocyclic ring, and each of them is preferably a ring little in reaction activity for the purpose of increasing stability of the platinum complex. A benzene ring, a pyridine ring, a pyrazine ring, a pyrimidine ring, and a pyridazine ring are preferred, more preferably a benzene ring, a pyridine ring, and a pyrazine ring are exemplified, still more preferably a benzene ring and a pyridine ring, and most preferably a benzene ring.

Each of $R_{21}$, $R_{22}$, $R_{23}$ and $R_{24}$ has the same meaning as that of $R_1$, $R_2$, $R_3$ and $R_4$ in formula (I), and the preferred range is also the same.

Each of $Z_{21}$, $Z_{22}$, $Z_{23}$ and $Z_{24}$ has the same meaning as $Z_{11}$, $Z_{12}$, $Z_{13}$ and $Z_{14}$ in formula (II). Each of ring $Q_7$ and $Q_8$ has the same meaning as $Q_3$ and $Q_4$ in formula (II), and the preferred range is also the same.

$A_3$ has the same meaning as $A_1$ in formula (I), and the preferred range is also the same.

Formula (IV) will be described below.

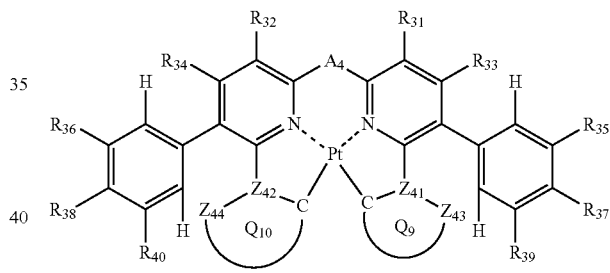

Formula (IV)

In formula (IV), each of $Z_{41}$, $Z_{42}$, $Z_{43}$ and $Z_{44}$ independently represents a carbon atom or a nitrogen atom, each of ring $Q_9$ containing a carbon atom, $Z_{41}$ and $Z_{43}$ and ring $Q_{10}$ containing a carbon atom, $Z_{42}$ and $Z_{44}$ independently represents an aromatic ring or an aromatic heterocylic ring, each of a bond for bonding $Z_{41}$ to the carbon atom coordinating to Pt contained in ring $Q_9$, a bond for bonding $Z_{41}$ to $Z_{43}$, a bond for bonding $Z_{42}$ to the carbon atom coordinating to Pt contained in ring $Q_{10}$, and a bond for bonding $Z_{42}$ to $Z_{44}$ independently represents a single bond or a double bond, provided that when $Z_{41}$ represents a nitrogen atom, each of the bond for bonding $Z_{41}$ to the carbon atom coordinating to Pt contained in ring $Q_9$ and the bond for bonding $Z_{41}$ to $Z_{43}$ represents a single bond, and when $Z_{42}$ represents a nitrogen atom, each of the bond for bonding $Z_{42}$ to the carbon atom coordinating to Pt contained in ring $Q_{10}$ and the bond for bonding $Z_{42}$ to $Z_{44}$ represents a single bond, and $Z_{43}$ and $Z_{44}$ do not have a substituent; each of $R_{31}$, $R_{32}$, $R_{33}$, $R_{34}$, $R_{35}$, $R_{36}$, $R_{37}$, $R_{38}$, $R_{39}$ and $R_{40}$ independently represents a hydrogen atom or a substituent; and $A_4$ represents a single bond or a divalent linking group.

In formula (IV), each of $R_{31}$, $R_{32}$, $R_{33}$ and $R_{34}$ has the same meaning as that of $R_1$, $R_2$, $R_3$ and $R_4$ in formula (I), and the preferred range is also the same.

As the examples of the substituents represented by $R_{35}$, $R_{36}$, $R_{37}$, $R_{38}$, $R_{39}$ and $R_{40}$, the substituents selected from substituent group B can be exemplified. As the substituents represented by $R_{35}$, $R_{36}$, $R_{37}$, $R_{38}$, $R_{39}$ and $R_{40}$, a hydrogen atom, an alkyl group, an aryl group, an amino group, an alkoxyl group, an aryloxy group, an acyl group, an alkoxycarbonyl group, an alkylthio group, a sulfonyl group, a hydroxyl group, a halogen atom, a cyano group, a nitro group, and a heterocyclic group are preferred, a hydrogen atom, an alkyl group, an aryl group, a halogen atom, a cyano group, and a heterocyclic group are more preferred, a hydrogen atom, a methyl group, a t-butyl group, a trifluoromethyl group, a phenyl group, a fluorine atom, a cyano group, and a pyridyl group are still more preferred, a hydrogen atom, a trifluoromethyl group, a fluorine atom, and a cyano group are still further preferred, a hydrogen atom and a cyano group are yet further preferred, and a hydrogen atom is especially preferred.

Each of $Z_{41}$, $Z_{42}$, $Z_{43}$ and $Z_{44}$ has the same meaning as $Z_{11}$, $Z_{12}$, $Z_{13}$ and $Z_{14}$ in formula (II). Each of ring $Q_9$ and $Q_{10}$ has the same meaning as $Q_3$ and $Q_4$ in formula (II), and the preferred range is also the same.

$A_4$ has the same meaning as $A_1$ in formula (I), and the preferred range is also the same.

Formula (V) will be described below.

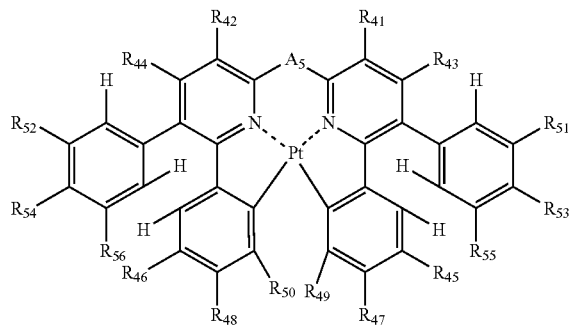

Formula (V)

In formula (V), each of $R_{41}$, $R_{42}$, $R_{43}$, $R_{44}$, $R_{45}$, $R_{46}$, $R_{47}$, $R_{48}$, $R_{49}$, $R_{50}$, $R_{51}$, $R_{52}$, $R_{53}$, $R_{54}$, $R_{55}$ and $R_{56}$ independently represents a hydrogen atom or a substituent; and $A_5$ represents a single bond or a divalent linking group.

In formula (V), each of $R_{41}$, $R_{42}$, $R_{43}$ and $R_{44}$ has the same meaning as that of $R_1$, $R_2$, $R_3$ and $R_4$ in formula (I), and the preferred range is also the same.

Each of $R_{51}$, $R_{52}$, $R_{53}$, $R_{54}$, $R_{55}$ and $R_{56}$ has the same meaning as that of $R_{35}$, $R_{36}$, $R_{37}$, $R_{38}$, $R_{39}$ and $R_{40}$ in formula (IV), and the preferred range is also the same.

As the examples of the substituents represented by $R_{45}$, $R_{46}$, $R_{47}$, $R_{48}$, $R_{49}$ and $R_{50}$, the substituents selected from substituent group B can be exemplified. As the substituents represented by $R_{45}$, $R_{46}$, $R_{47}$, $R_{48}$, $R_{49}$ and $R_{50}$, a hydrogen atom, an alkyl group, an aryl group, an amino group, an alkoxyl group, an aryloxy group, an acyl group, an alkoxycarbonyl group, an alkylthio group, a sulfonyl group, a hydroxyl group, a halogen atom, a cyano group, a nitro group, and a heterocyclic group are preferred, a hydrogen atom, an alkyl group, an aryl group, a halogen atom, a cyano group, and a heterocyclic group are more preferred, a hydrogen atom, a methyl group, a t-butyl group, a trifluoromethyl group, a phenyl group, a fluorine atom, a cyano group, and a pyridyl group are still more preferred, a hydrogen atom, a trifluoromethyl group, a phenyl group, a fluorine atom, and a cyano group are still further preferred, a hydrogen atom, a trifluoromethyl group, a phenyl group, and a cyano group are still yet more preferred, and a hydrogen atom and a cyano group are especially preferred. $R_{45}$, $R_{46}$, $R_{47}$, $R_{48}$, $R_{49}$ and $R_{50}$ may be bonded to each other to form a ring, if possible.

$A_5$ has the same meaning as that of $A_1$ in formula (I), and the preferred range is also the same.

Formula (VI) will be described below.

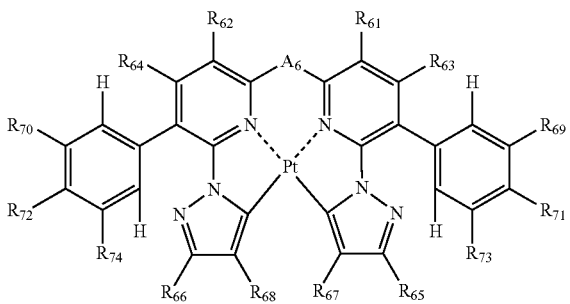

Formula (VI)

In formula (VI), each of $R_{61}$, $R_{62}$, $R_{63}$, $R_{64}$, $R_{65}$, $R_{66}$, $R_{67}$, $R_{68}$, $R_{69}$, $R_{70}$, $R_{71}$, $R_{72}$, $R_{73}$ and $R_{74}$ independently represents a hydrogen atom or a substituent; and $A_6$ represents a single bond or a divalent linking group.

In formula (VI), each of $R_{61}$, $R_{62}$, $R_{63}$ and $R_{64}$ has the same meaning as that of $R_1$, $R_2$, $R_3$ and $R_4$ in formula (I), and the preferred range is also the same.

Each of $R_{69}$, $R_{70}$, $R_{71}$, $R_{72}$, $R_{73}$ and $R_{74}$ has the same meaning as that of $R_{35}$, $R_{36}$, $R_{37}$, $R_{38}$, $R_{39}$ and $R_{40}$ in formula (IV), and the preferred range is also the same.

As the examples of the substituents represented by $R_{65}$, $R_{66}$, $R_{67}$ and $R_{68}$, substituent group B can be exemplified. As the substituents represented by $R_{65}$, $R_{66}$, $R_{67}$ and $R_{68}$, a hydrogen atom, an alkyl group, an aryl group, an amino group, an alkoxyl group, an aryloxy group, an acyl group, an alkoxycarbonyl group, an alkylthio group, a sulfonyl group, a hydroxyl group, a halogen atom, a cyano group, a nitro group, and a heterocyclic group are preferred, a hydrogen atom, an alkyl group, an aryl group, a halogen atom, a cyano group, and a heterocyclic group are more preferred, a hydrogen atom, a methyl group, a t-butyl group, a trifluoromethyl group, a phenyl group, a fluorine atom, a cyano group, and a pyridyl group are still more preferred, a hydrogen atom, a trifluoromethyl group, a fluorine atom, and a cyano group are still further preferred, a hydrogen atom, a trifluoromethyl group, and a cyano group are still yet further preferred, and a trifluoromethyl group and a cyano group are still further preferred, and a trifluoromethyl group is especially preferred. $R_{65}$, $R_{66}$, $R_{67}$ and $R_{68}$ may be bonded to each other to form a ring, if possible.

$A_6$ has the same meaning as that of $A_1$ in formula (I), and the preferred range is also the same.

Formula (VII) will be described below.

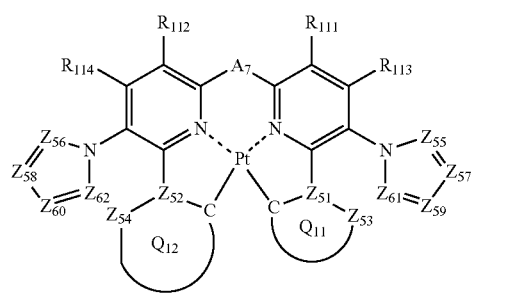

Formula (VIII)

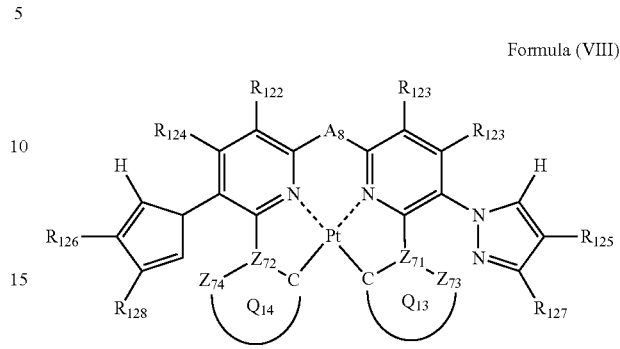

Formula (VIII)

In formula (VII), each of $Z_{55}$, $Z_{56}$, $Z_{57}$, $R_{58}$, $R_{59}$, $R_{60}$, $R_{61}$ and $Z_{62}$ independently represents a carbon atom or a nitrogen atom, and $Z_{55}$, $Z_{56}$, $R_{61}$ and $Z_{62}$ do not have a substituent; each of $Z_{51}$, $Z_{52}$, $Z_{53}$ and $Z_{54}$ independently represents a carbon atom or a nitrogen atom, each of ring $Q_{11}$ containing a carbon atom, $Z_{51}$ and $Z_{53}$ and ring $Q_{12}$ containing a carbon atom, $Z_{52}$ and $Z_{54}$ independently represents an aromatic ring or an aromatic heterocylic ring, each of a bond for bonding $Z_{51}$ to the carbon atom coordinating to Pt contained in ring $Q_{11}$, a bond for bonding $Z_{51}$ to $Z_{53}$, a bond for bonding $Z_{52}$ to the carbon atom coordinating to Pt contained in ring $Q_{12}$, and a bond for bonding $Z_{52}$ to $Z_{54}$ independently represents a single bond or a double bond, provided that when $Z_{51}$ represents a nitrogen atom, each of the bond for bonding $Z_{51}$ to the carbon atom coordinating to Pt contained in ring $Q_{11}$ and the bond for bonding $Z_{51}$ to $Z_{53}$ represents a single bond, and when $Z_{52}$ represents a nitrogen atom, each of the bond for bonding $Z_{52}$ to the carbon atom coordinating to Pt contained in ring $Q_{12}$ and the bond for bonding $Z_{52}$ to $Z_{54}$ represents a single bond, and $Z_{53}$ and $Z_{54}$ do not have a substituent; each of $R_{111}$, $R_{112}$, $R_{113}$ and $R_{114}$ independently represents a hydrogen atom or a substituent; and $A_7$ represents a single bond or a divalent linking group.

Each of a 5-membered ring formed by a nitrogen atom, $Z_{55}$, $Z_{57}$, $R_{59}$ and $R_{61}$, and a 5-membered ring formed by a nitrogen atom, $Z_{56}$, $R_{58}$, $R_{60}$ and $Z_{62}$ is preferably a ring little in reaction activity for the purpose of increasing stability of the platinum complex. A pyrrole ring, a pyrazole ring, an imidazole ring, and a triazole ring are preferred, a pyrrole ring, a pyrazole ring, and an imidazole ring are more preferred, a pyrazole ring and an imidazole ring are still more preferred, and, a pyrazole ring is most preferred.

Each of $R_{111}$, $R_{112}$, $R_{113}$ and $R_{114}$ has the same meaning as that of $R_1$, $R_2$, $R_3$ and $R_4$ in formula (I), and the preferred range is also the same.

Each of $Z_{51}$, $Z_{52}$, $Z_{53}$ and $Z_{54}$ has the same meaning as $Z_{11}$, $Z_{12}$, $Z_{13}$ and $Z_{14}$ in formula (II). Each of ring $Q_{11}$ and $Q_{12}$ has the same meaning as $Q_3$ and $Q_4$ in formula (II), and the preferred range is also the same.

$A_7$ has the same meaning as $A_1$ in formula (I), and the preferred range is also the same.

Formula (VIII) will be described below.

In formula (VIII), each of $Z_{71}$, $Z_{72}$, $Z_{73}$ and $Z_{74}$ independently represents a carbon atom or a nitrogen atom, each of ring $Q_{13}$ containing a carbon atom, $Z_{71}$ and $Z_{73}$ and ring $Q_{14}$ containing a carbon atom, $Z_{72}$ and $Z_{74}$ independently represents an aromatic ring or an aromatic heterocyclic ring, each of a bond for bonding $Z_{71}$ to the carbon atom coordinating to Pt contained in ring $Q_{13}$, a bond for bonding $Z_{71}$ to $Z_{73}$, a bond for bonding $Z_{72}$ to the carbon atom coordinating to Pt contained in ring $Q_{14}$, and a bond for bonding $Z_{72}$ to $Z_{74}$ independently represents a single bond or a double bond, provided that when $Z_{71}$ represents a nitrogen atom, each of the bond for bonding $Z_{71}$ to the carbon atom coordinating to Pt contained in ring $Q_{13}$ and the bond for bonding $Z_{71}$ to $Z_{73}$ represents a single bond, and when $Z_{72}$ represents a nitrogen atom, each of the bond for bonding $Z_{72}$ to the carbon atom coordinating to Pt contained in ring $Q_{14}$ and the bond for bonding $Z_{72}$ to $Z_{74}$ represents a single bond, and $Z_{73}$ and $Z_{74}$ do not have a substituent; each of $R_{121}$, $R_{122}$, $R_{123}$, $R_{124}$, $R_{125}$, $R_{126}$, $R_{127}$ and $R_{128}$ independently represents a hydrogen atom or a substituent; and $A_8$ represents a single bond or a divalent linking group.

In formula (VIII), each of $R_{121}$, $R_{122}$, $R_{123}$ and $R_{124}$ has the same meaning as that of $R_1$, $R_2$, $R_3$ and $R_4$ in formula (I), and the preferred range is also the same.

As the examples of the substituents represented by $R_{125}$, $R_{126}$, $R_{127}$ and $R_{128}$, substituent group B can be exemplified. As the substituents represented by $R_{125}$, $R_{126}$, $R_{127}$ and $R_{128}$, a hydrogen atom, an alkyl group, an aryl group, an amino group, an alkoxyl group, an aryloxy group, an acyl group, an alkoxycarbonyl group, an alkylthio group, a sulfonyl group, a hydroxyl group, a halogen atom, a cyano group, a nitro group, and a heterocyclic group are preferred, a hydrogen atom, an alkyl group, an aryl group, a halogen atom, a cyano group, and a heterocyclic group are more preferred, a hydrogen atom, a methyl group, a t-butyl group, a trifluoromethyl group, a phenyl group, a fluorine atom, a cyano group, and a pyridyl group are still more preferred, a hydrogen atom, a trifluoromethyl group, a fluorine atom, and a cyano group are still further preferred, a hydrogen atom, a trifluoromethyl group, and a cyano group are yet further preferred, and a hydrogen atom and a trifluoromethyl group are especially preferred.

Each of $Z_{71}$, $Z_{72}$, $Z_{73}$ and $Z_{74}$ has the same meaning as $Z_{11}$, $Z_{12}$, $Z_{13}$ and $Z_{14}$ in formula (II). Each of ring $Q_{13}$ and $Q_{14}$ has the same meaning as $Q_3$ and $Q_4$ in formula (II), and the preferred range is also the same.

$A_8$ has the same meaning as $A_1$ in formula (I), and the preferred range is also the same.

Formula (IX) will be described below.

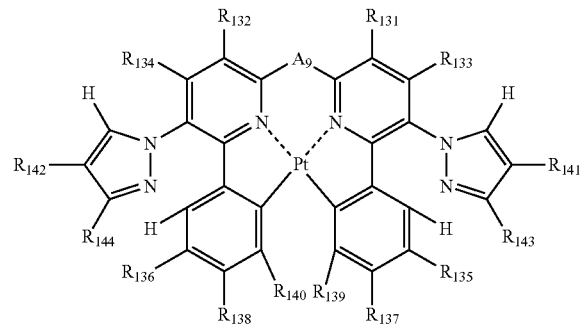

Formula (IX)

In formula (IX), each of $R_{131}$, $R_{132}$, $R_{133}$, $R_{134}$, $R_{135}$, $R_{136}$, $R_{137}$, $R_{138}$, $R_{139}$, $R_{140}$, $R_{141}$, $R_{142}$, $R_{143}$ and $R_{144}$ independently represents a hydrogen atom or a substituent; and $A_9$ represents a single bond or a divalent linking group.

In formula (IX), each of $R_{131}$, $R_{132}$, $R_{133}$ and $R_{134}$ has the same meaning as that of $R_1$, $R_2$, $R_3$ and $R_4$ in formula (I), and the preferred range is also the same.

Each of $R_{141}$, $R_{142}$, $R_{143}$ and $R_{144}$ has the same meaning as that of $R_{125}$, $R_{126}$, $R_{127}$ and $R_{128}$ in formula (VIII), and the preferred range is also the same.

Each of $R_{135}$, $R_{136}$, $R_{137}$, $R_{138}$, $R_{139}$ and $R_{140}$ has the same meaning as that of $R_{45}$, $R_{46}$, $R_{47}$, $R_{48}$, $R_{49}$ and $R_{50}$ in formula (V), and the preferred range is also the same.

$A_9$ has the same meaning as that of $A_1$ in formula (I), and the preferred range is also the same.

Formula (X) will be described below.

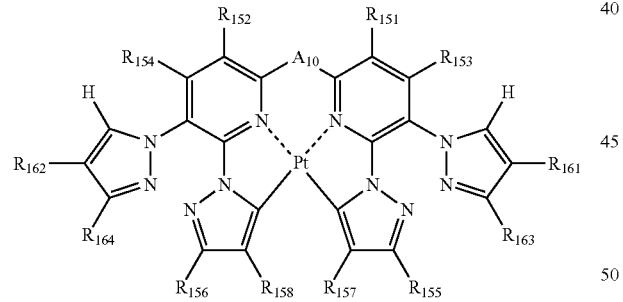

Formula (X)

In formula (X), each of $R_{151}$, $R_{152}$, $R_{153}$, $R_{154}$, $R_{155}$, $R_{156}$, $R_{157}$, $R_{158}$, $R_{161}$, $R_{162}$, $R_{163}$ and $R_{164}$ independently represents a hydrogen atom or a substituent; and $A_{10}$ represents a single bond or a divalent linking group.

In formula (X), each of $R_{151}$, $R_{152}$, $R_{153}$ and $R_{154}$ has the same meaning as $R_1$, $R_2$, $R_3$ and $R_4$ in formula (I), and the preferred range is also the same.

Each of $R_{161}$, $R_{162}$, $R_{163}$ and $R_{164}$ has the same meaning as $R_{125}$, $R_{126}$, $R_{127}$ and $R_{128}$ in formula (VIII), and the preferred range is also the same.

Each of $R_{155}$, $R_{156}$, $R_{157}$ and $R_{158}$ has the same meaning as $R_{65}$, $R_{66}$, $R_{67}$ and $R_{68}$ in formula (VI), and the preferred range is also the same.

$A_{10}$ has the same meaning as that of $A_1$ in formula (I), and the preferred range is also the same.

The platinum complex represented by any of formulae (I), (II), (III), (IV), (V), (VI), (VII), (VIII), (IX) and (X) may be a high molecular weight compound having the compound of the invention in the main chain or side chain. The weight average molecular weight of the platinum complex is preferably 2,000 or higher.

The specific examples of the complexes represented by any of formulae (I), (II), (III), (IV), (V), (VI), (VII), (VIII), (IX) and (X) are shown below, but the invention is not restricted thereto.

1

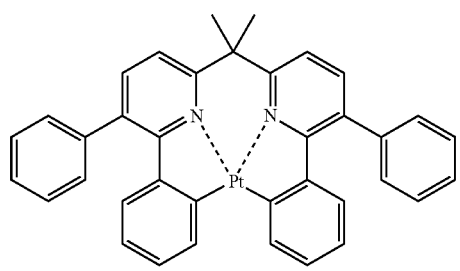

2

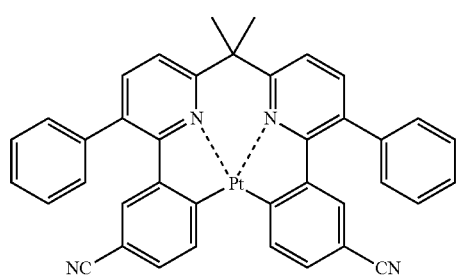

3

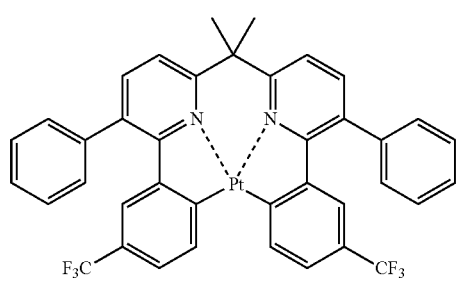

4

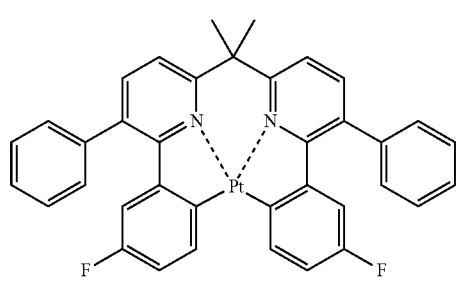

-continued
5
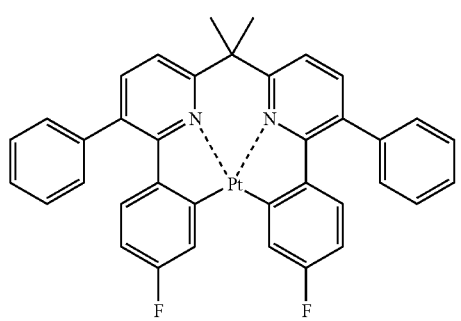
6
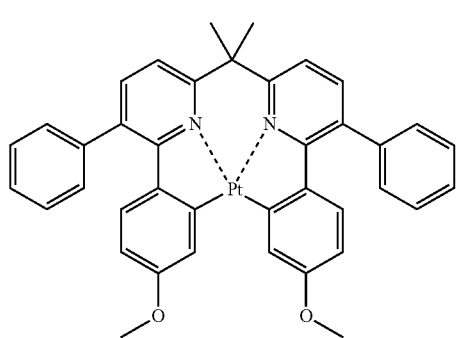
7
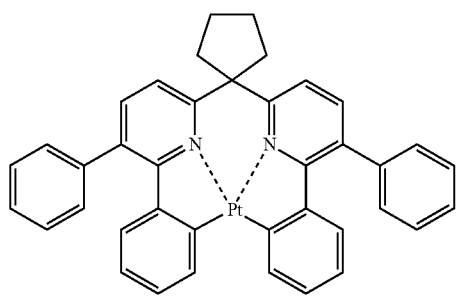
8
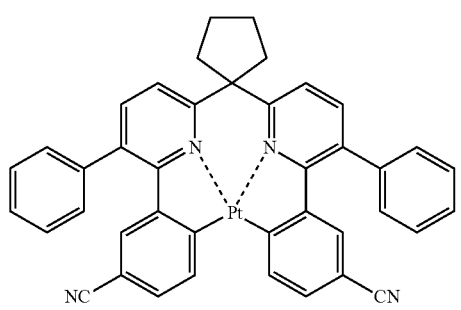
9
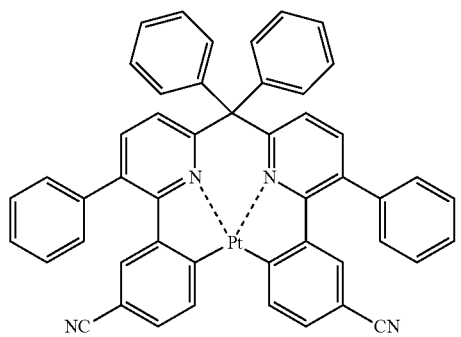
-continued
10
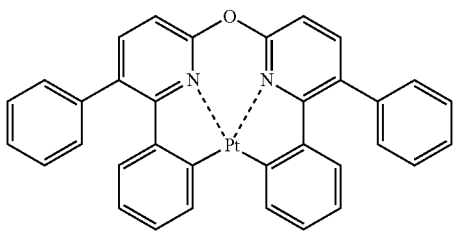
11
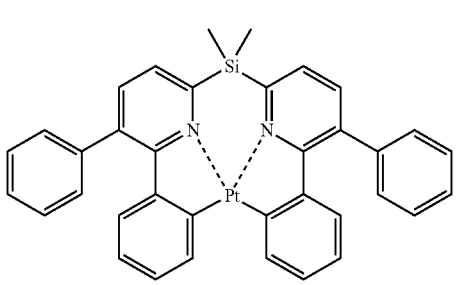
12
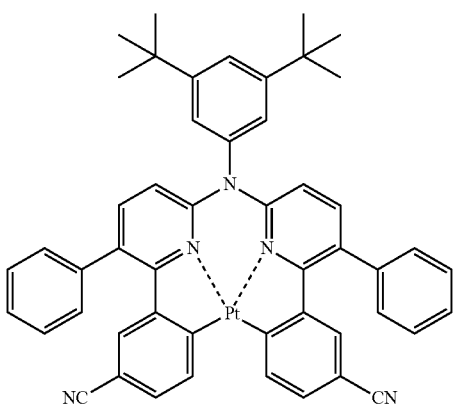
13
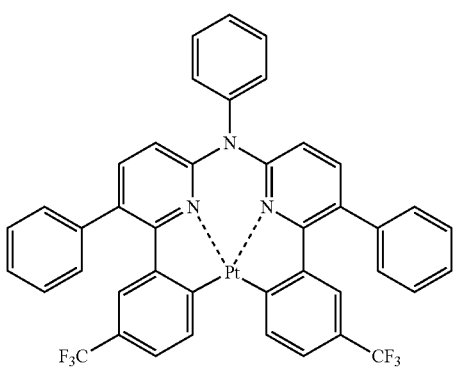

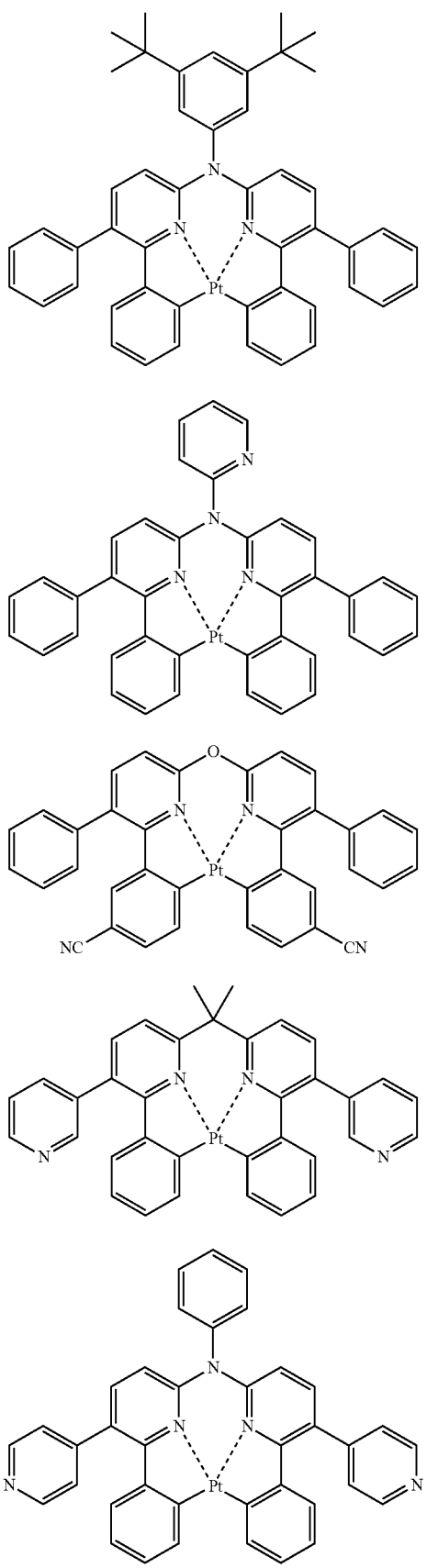
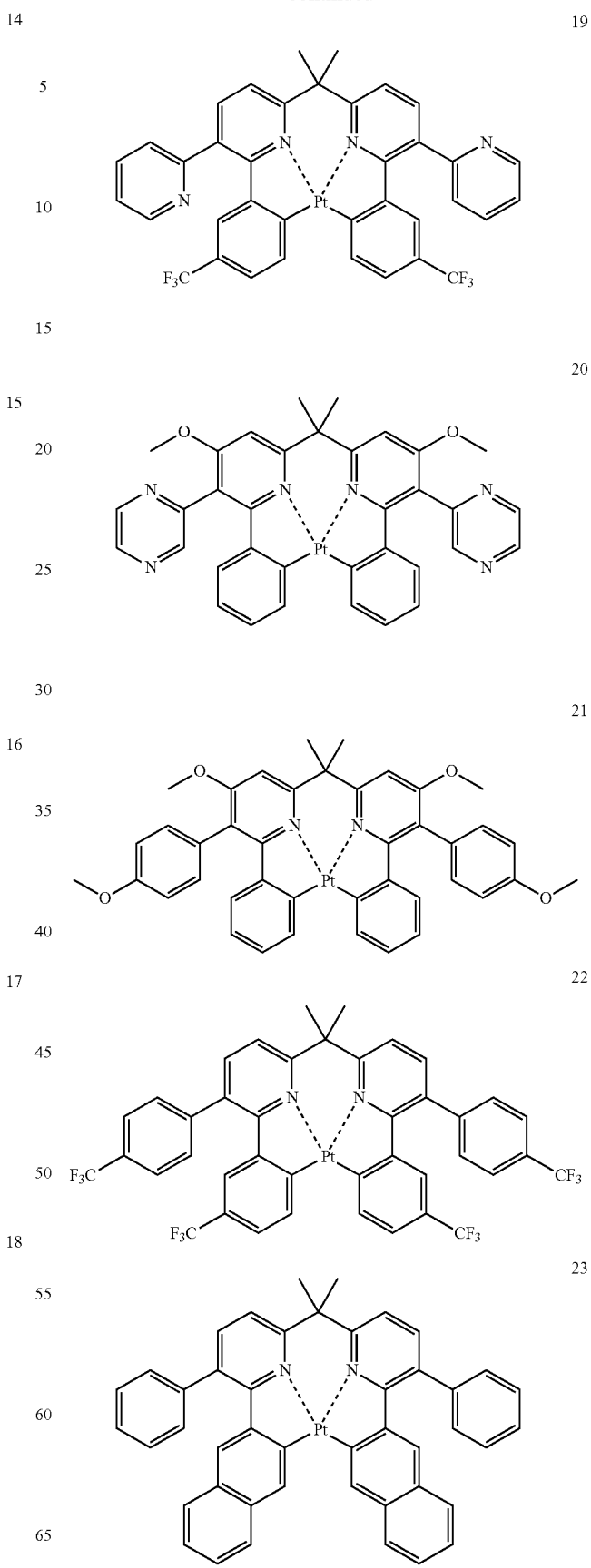

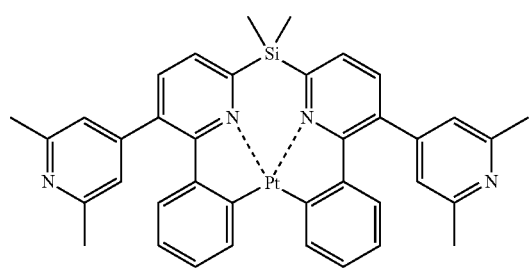
24
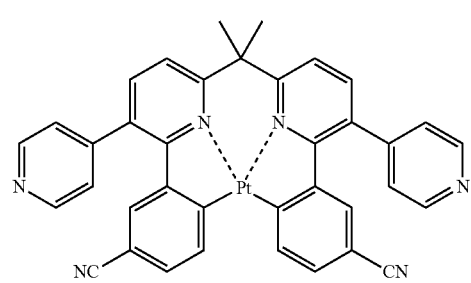
25
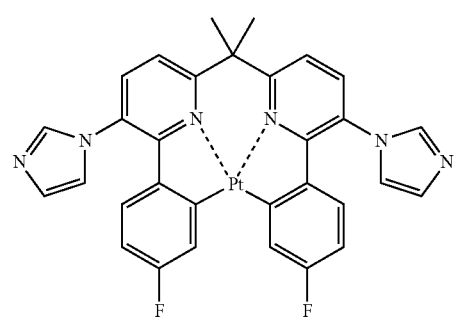
26
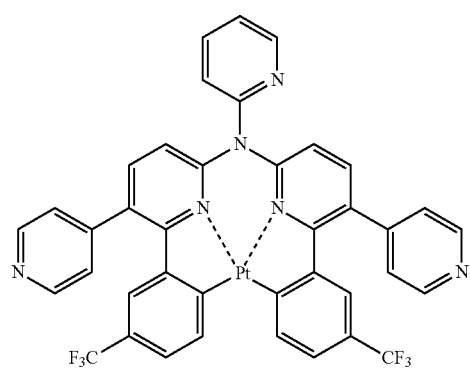
27
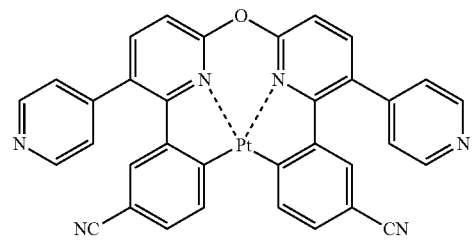
29
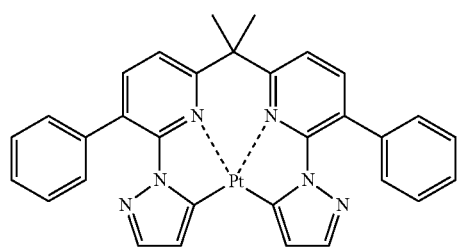
30
31
32
33

34
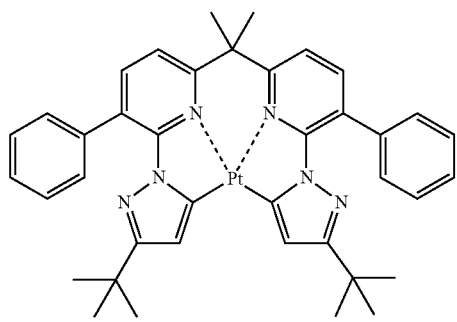
35
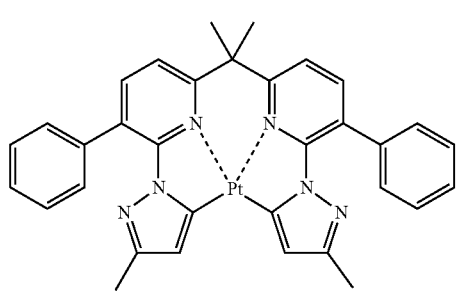
36
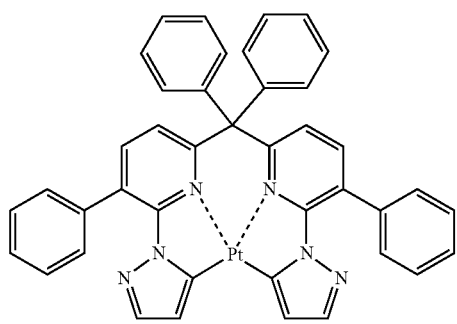
37
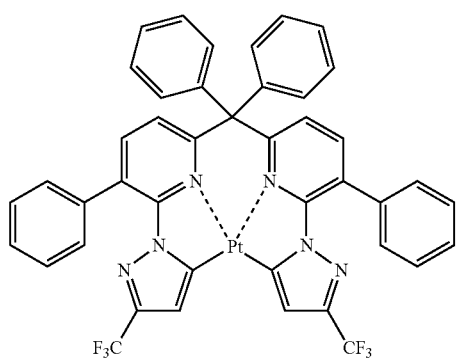
38
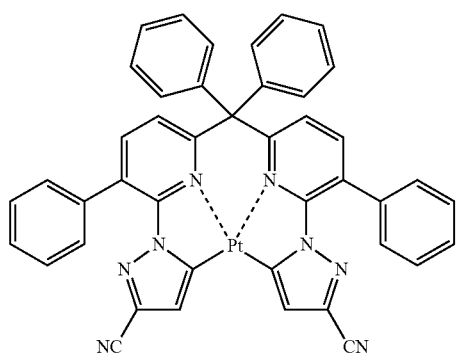
39
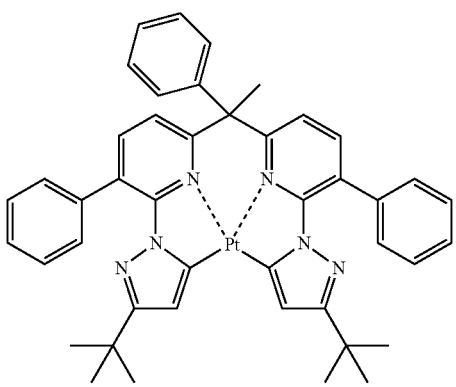
40
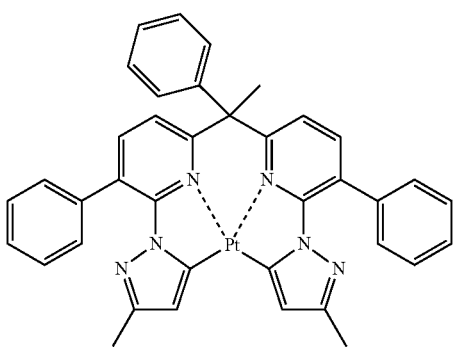
41
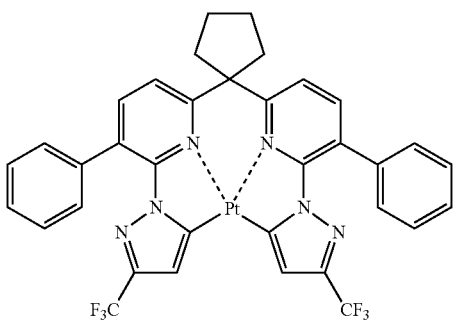
42
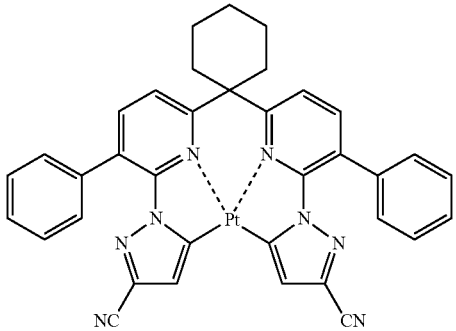

43
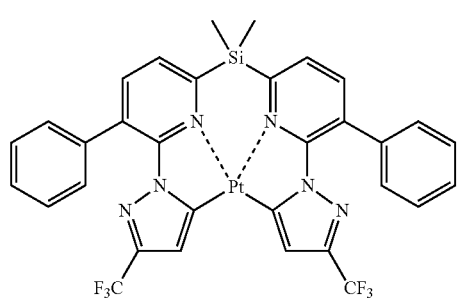
44
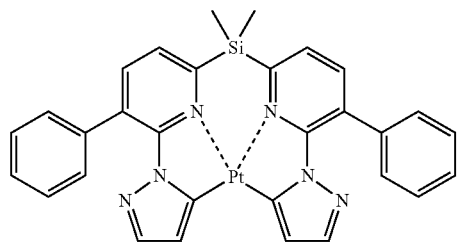
45
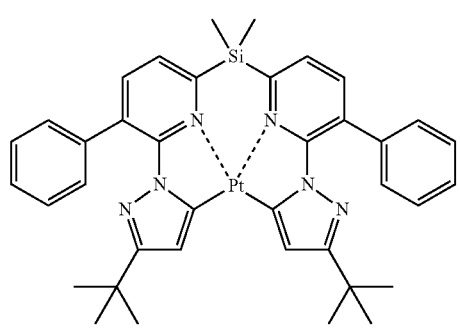
46
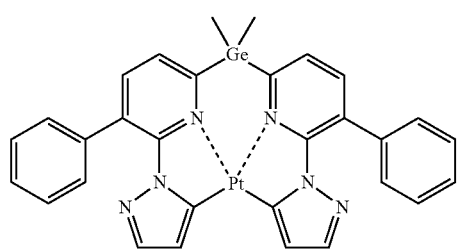
47
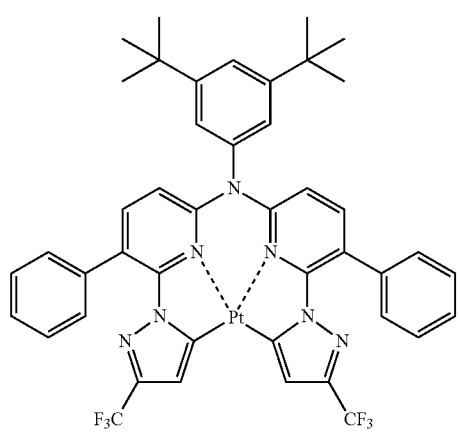
48
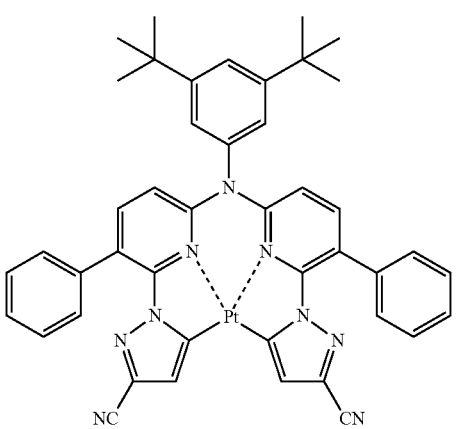
49
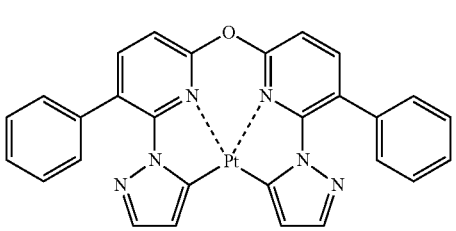
50
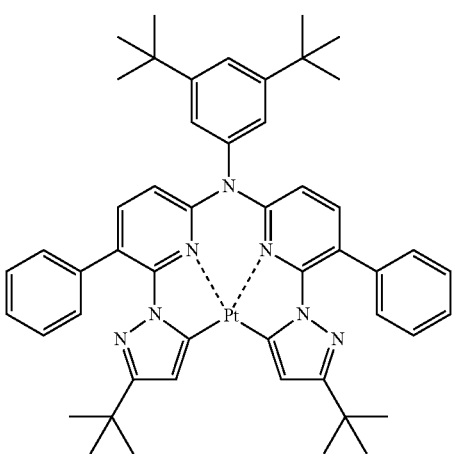
51
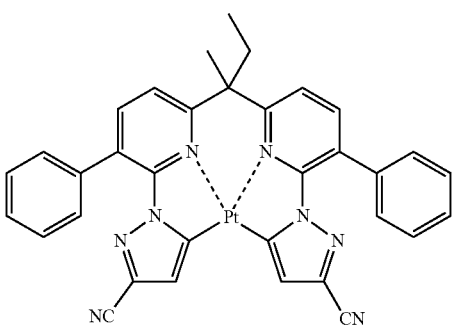

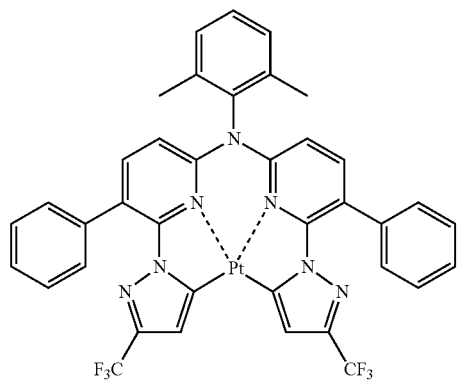
52
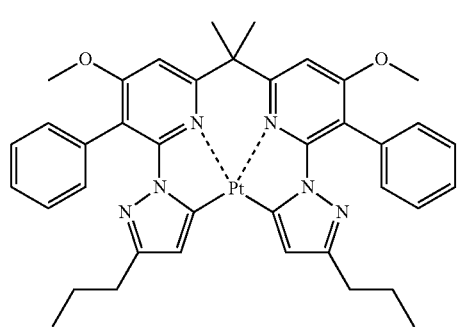
53
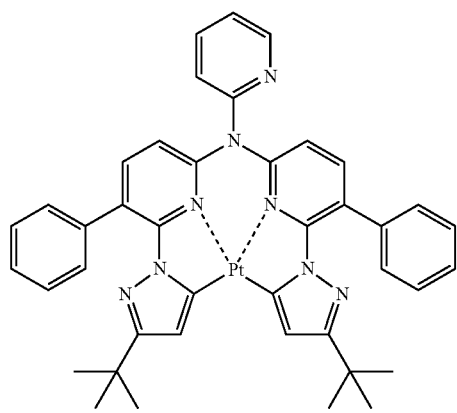
54
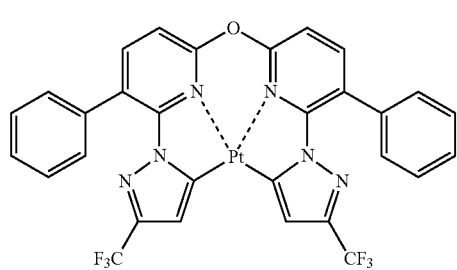
55
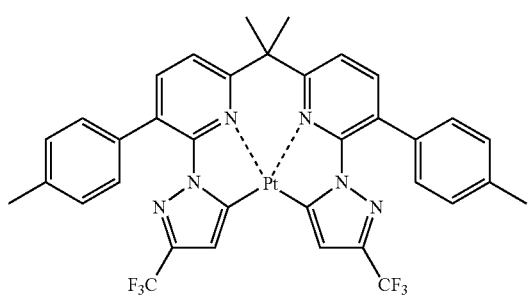
56
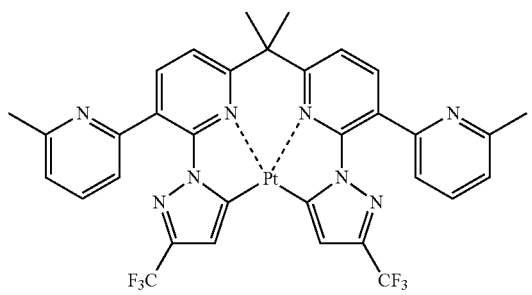
57
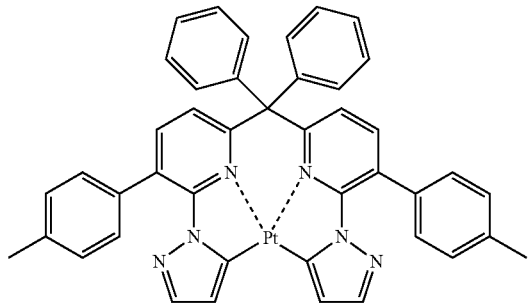
58
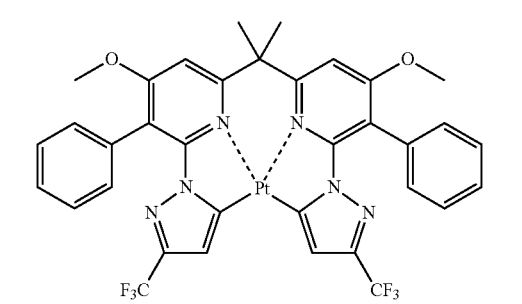
59
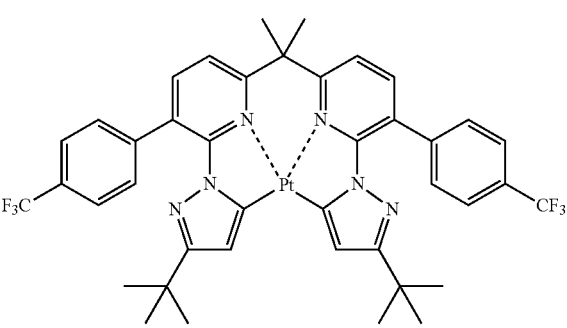
60

-continued
61
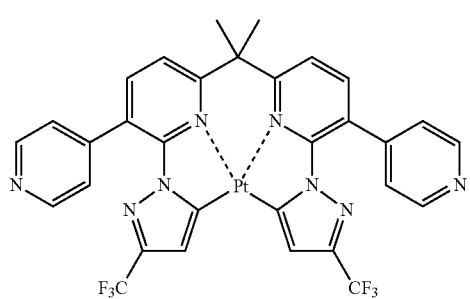
62
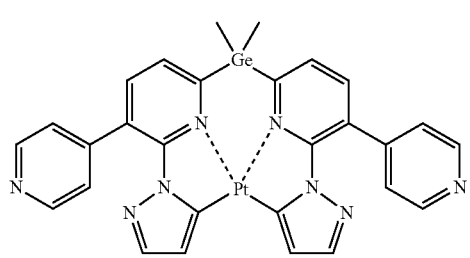
63
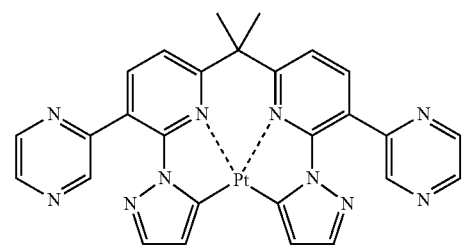
64
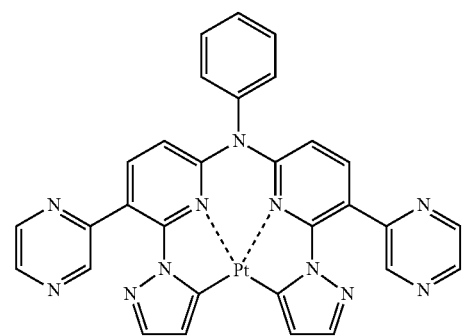
65
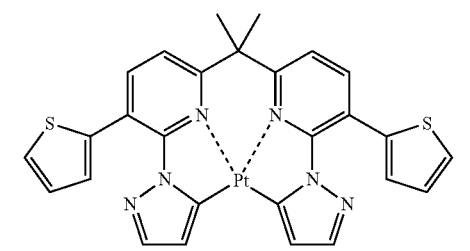
-continued
66
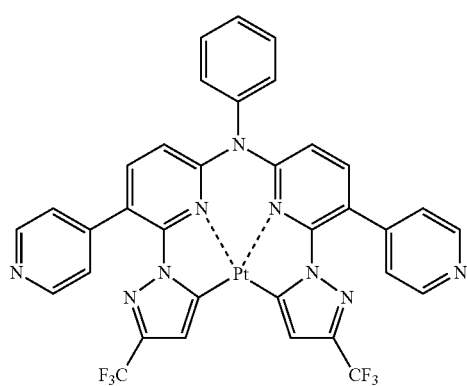
67
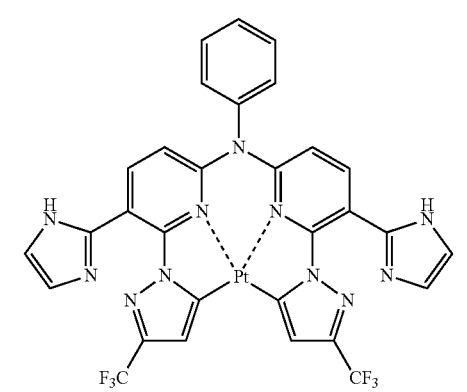
68
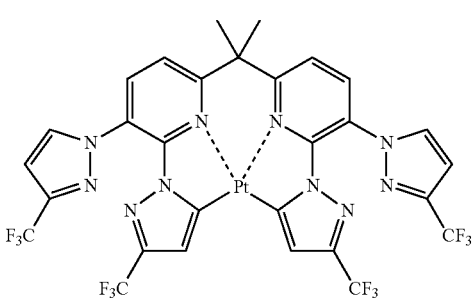
69
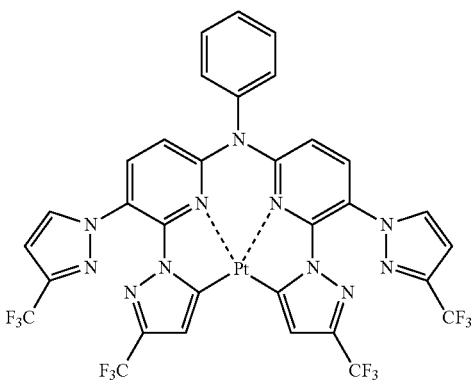

-continued

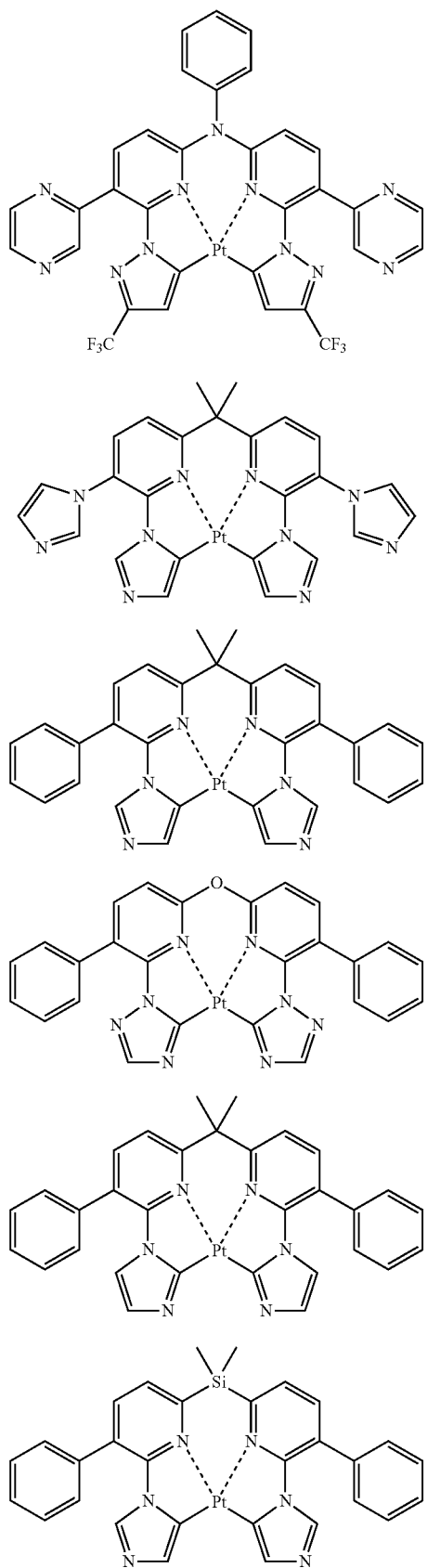

The complexes in the invention can be manufactured, for example, according to the processes shown below. The manufacturing method of Compound (E-1) shown below will be specifically described.

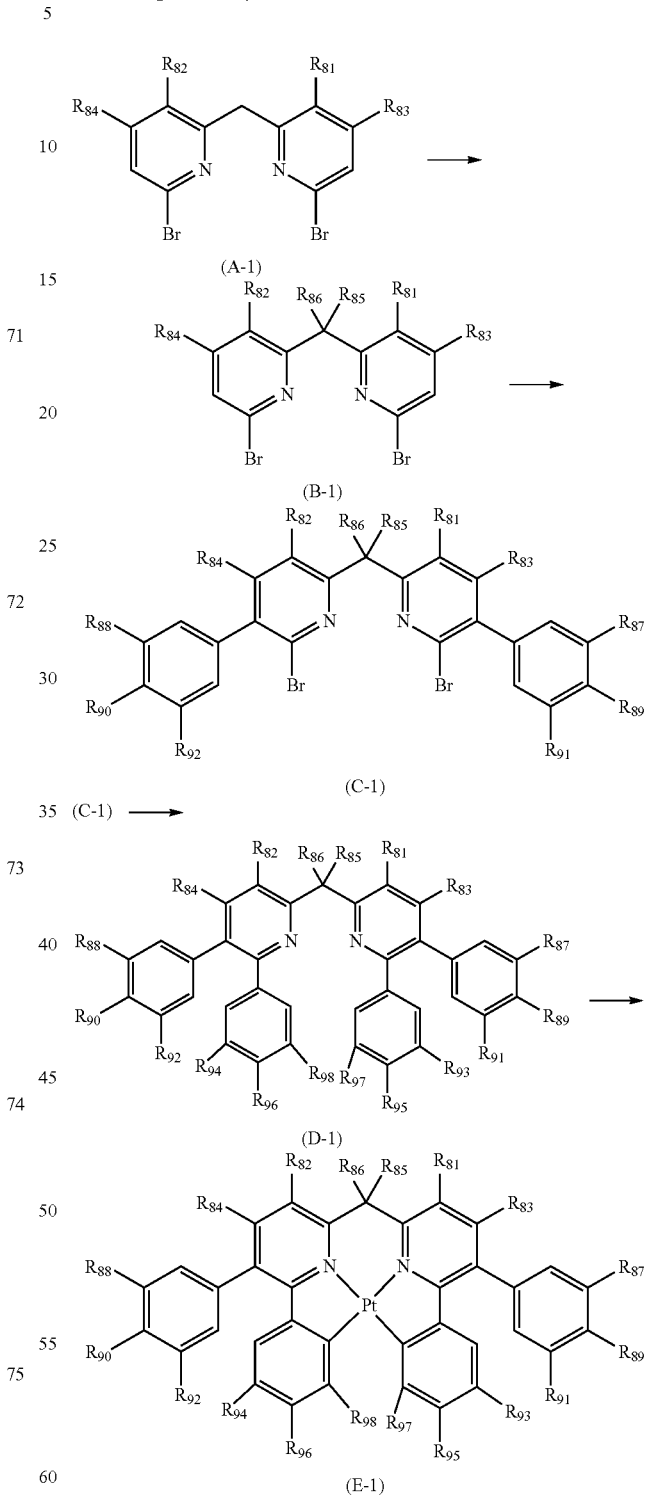

In the above formulae, each of $R_{81}$, $R_{82}$, $R_{83}$, $R_{84}$, $R_{87}$, $R_{88}$, $R_{89}$, $R_{90}$, $R_{91}$, $R_{92}$, $R_{93}$, $R_{94}$, $R_{95}$, $R_{96}$, $R_{97}$ and $R_{98}$ has the same meaning as $R_{41}$, $R_{42}$, $R_{43}$, $R_{44}$, $R_{51}$, $R_{52}$, $R_{53}$, $R_{54}$, $R_{55}$, $R_{56}$, $R_{45}$, $R_{46}$, $R_{47}$, $R_{48}$, $R_{49}$ and $R_{50}$ in formula (V). $R_{85}$ and $R_{86}$ have the same meaning as substituent group B.

The complex of the invention can be obtained according to the methods described in G. R. Newkome et al., *Journal of Organic Chemistry*, 53, 786 (1988), page 789, from left column line 53 to right column line 7, page 790, from left column lines 18 to 38, page 790, from right column lines 19 to 30, and combination of these methods. With Compound (A-1) being a starting material, from 1 to 1.2 equivalent weight of bases such as lithium diisopropylamide, potassium t-butoxide, sodium hydroxide, etc., are added to an N,N-dimethylformamide solution of (A-1) at 0° C. to room temperature, and the reaction mixture is reacted at 0° C. to room temperature for 30 minutes or so, from 1.5 to 4 equivalent weight of alkyl halide represented by $R_{85}X$ (X represents halogen) is added to the above reaction solution, the solution is reacted at room temperature for 30 minutes or so to be monoalkylated, and then again on the same condition, from 1 to 1.2 equivalent weight of the above bases and an excess amount of alkyl halide $R_{86}X$ (X represents halogen) are reacted, thus dialkyl substitution product (B-1) can be obtained in a yield of from 70 to 99%.

With Compound (B-1) being a starting material, from 2.4 to 3.0 equivalent weight of lithium diisopropylamide is added to a tetrahydrofuran solution of (B-1) at −50 to −80° C., and then from 2.4 to 3.0 equivalent weight of zinc chloride or trialkyltin chloride, followed by Negishi coupling reaction or Stille coupling reaction with phenyl halide in the presence of a palladium catalyst, thus (C-1) can be synthesized.

(D-1) can be synthesized from (C-1) according to the method described in *Synth. Commun.*, 11, 513 (1981).

Compound (E-1) of the invention can be synthesized by dissolving Compound (D-1) and from 1 to 1.5 equivalent weight of platinous chloride in benzonitrile, heating the resulted solution at 130° C. to heat-refluxing temperature (the boiling point of benzonitrile: 191° C.) and stirring for 30 minutes to 4 hours. Compound (E-1) can be refined by recrystallization using chloroform or ethyl acetate, silica gel column chromatography, and sublimation refining.

A complex represented by the following formula (E-2) can be synthesized by the following manufacturing method.

(C-1) ⟶

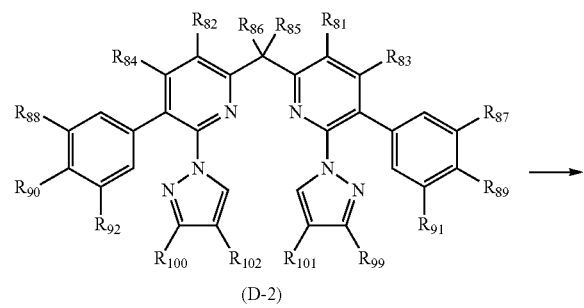

(D-2)

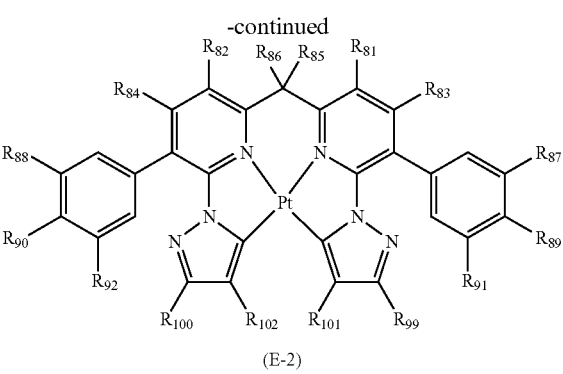

(E-2)

In the above formulae, each of $R_{81}$, $R_{82}$, $R_{83}$, $R_{84}$, $R_{87}$, $R_{88}$, $R_{89}$, $R_{90}$, $R_{91}$, $R_{92}$, $R_{99}$, $R_{100}$, $R_{101}$ and $R_{102}$ has the same meaning as $R_{61}$, $R_{62}$, $R_{63}$, $R_{64}$, $R_{69}$, $R_{70}$, $R_{71}$, $R_{72}$, $R_{73}$, $R_{74}$, $R_{65}$, $R_{66}$, $R_{67}$ and $R_{68}$ in formula (VI). $R_{85}$ and $R_{86}$ have the same meaning as substituent group B.

(D-2) can be synthesized from (C-1) according to the methods described in *Chem. Ber.*, 113, 2749 (1980) and *Eur. J. Org. Chem.*, 4, 695 (2004).

Compound (E-2) of the invention can be synthesized by dissolving Compound (D-2) and from 1 to 1.5 equivalent weight of platinous chloride in benzonitrile, heating the solution at 130° C. to heat-refluxing temperature (the boiling point of benzonitrile: 191° C.) and stirring for 30 minutes to 4 hours. Compound (E-2) can be refined by recrystallization using chloroform or ethyl acetate, silica gel column chromatography, and sublimation refining.

Incidentally, in the above manufacturing methods, when defined substituents are changed under the condition of a certain synthesis method or inappropriate in performing the synthesis method, manufacture is easily possible by means of protection of a functional group or release of a functional group as a protective group (e.g., T. W. Greene, *Protective Groups in Organic Synthesis*, John Wiley & Sons Inc. (1981)). Further, if necessary, it is also possible to arbitrarily change the order of reaction processes such as introduction of a substituent.

Organic Electroluminescence Device

The organic electroluminescence device in the invention will be described in detail below.

The organic electroluminescence device in the invention is an organic electroluminescence device comprising a pair of electrodes and at least one organic layer between the pair of electrodes, and at least one compound (I) is contained in the at least one organic layer.

When the organic compound layer consists of one layer, the device has a light-emitting layer as the organic compound layer. From the properties of the device, it is preferred that at least one electrode of the anode and the cathode is transparent or translucent.

The organic compound layer is not especially limited, and the device may have, besides the light-emitting layer, a hole-injecting layer, a hole-transporting layer, an electron injecting layer, an electron-transporting layer, a hole blocking layer, an electron-blocking layer, an exciton blocking layer, and a protective layer. Further, each of these layers may serve for other functions.

As the embodiment of lamination of the organic compound layers in the invention, an embodiment of lamination of the hole-transporting layer, the light-emitting layer and the electron-transporting layer from the anode side is preferred. Further, a charge-blocking layer may be provided between the hole-transporting layer and the light-emitting layer, or between the light-emitting layer and the electron transporting layer. The hole-injecting layer may be provided between the anode and the hole-transporting layer, or the electron injecting layer may be provided between the cathode and the electron-transporting layer. Incidentally, each of these layers may consist of a plurality of secondary layers.

When the organic compound layer consists of a plurality of layers, the complex of the invention may be contained in any layer. The complex of the invention is preferably contained in the light-emitting layer, more preferably contained in the light-emitting layer as light-emitting material or host material, still more preferably contained in the light-emitting layer as light-emitting material, and especially preferably contained in the light-emitting layer with at least one host material.

The content of a phosphorescent material usable in the invention (at least one of the complex of the invention and/or a phosphorescent material to be used in combination) is preferably 0.1 wt % or more and 50 wt % or less of the total mass of the light-emitting layer, more preferably 0.2 wt % or more and 50 wt % or less, still more preferably 0.3 wt % or more and 40 wt % or less, and most preferably 20 wt % or more and 30 wt % or less. In particular, when a phosphorescent material is used in the range of 20 wt % or more and 30 wt % or less, the chromaticity of light emission of the organic electroluminescence device is little in dependency on the addition concentration of the phosphorescent material.

It is most preferred for the organic electroluminescence device of the invention to contain at least on of compounds (I) (the complexes of the invention) in the proportion of from 20 to 30 wt % of the total mass of the light-emitting layer.

The host material is a compound primarily bearing injection and transportation of charge in a light-emitting layer, which is a compound that does not substantially emit light. In the specification of the invention, the terms "does not substantially emit light" means that the amount of light emission from the compound that does not substantially emit light is preferably 5% or less of the total amount of light emission of the device as a whole, more preferably 3% or less and still more preferably 1% or less.

The concentration of the host material in a light emitting layer is not especially restricted, but the host material is preferably the main component (the component the highest in content) in a light-emitting layer, more preferably 50 wt % or more and 99.9 wt % or less, still more preferably 50 wt % or more and 99.8 wt % or less, still yet preferably 60 wt % or more and 99.7 wt % or less, and most preferably 70 wt % or more and 80 wt % or less.

The glass transition point of the host material is preferably 100° C. or higher and 500° C. or lower, more preferably 110° C. or higher and 300° C. or lower, and still more preferably 120° C. or higher and 250° C. or lower.

The fluorescent wavelength of the host material contained in the light-emitting layer of the invention in the state of a film is preferably in the range of 400 nm or more and 650 nm or less, more preferably in the range of 420 nm or more and 600 nm or less, and still more preferably in the range of 440 nm or more and 550 nm or less.

As the host materials contained in the light-emitting layer of the invention, e.g., materials having a carbazole structure, materials having a diarylamine structure, materials having a pyridine structure, materials having a pyrazine structure, materials having a triazine structure, materials having an arylsilane structure, and materials described later in the items of hole-injecting layer, hole-transporting layer, electron-injecting layer and electron-transporting layer are exemplified.

As the host materials for use in the invention, e.g., the compounds disclosed in JP-A-2002-100476, paragraphs 0113 to 0161 and JP-A-2004-214179, paragraphs 0087 to 0098 can be preferably used, but the invention is not restricted to these compounds.

When the complex of the invention is introduced into the layers other than a light-emitting layer (e.g., a charge transporting layer, etc.), the content in the layer is preferably from 10 wt % to 100 wt %, and more preferably from 30 wt % to 100 wt %. Each element constituting the device of the invention will be described in detail below.

Substrate:

The substrate for use in the invention is preferably a substrate that does not scatter or attenuate the light emitted from the organic layers. The specific examples of the materials of the substrate include inorganic materials, e.g., yttria stabilized zirconia (YSZ), glass, etc., and organic materials, such as polyester, e.g., polyethylene terephthalate, polybutylene phthalate, polyethylene naphthalate, etc., polystyrene, polycarbonate, polyether sulfone, polyallylate, polyimide, polycycloolefin, norbornene resin, poly(chlorotrifluoroethylene), etc.

When glass is used as the substrate, non-alkali glass is preferably used as the material for reducing elution of ions from the glass. Further, when soda lime glass is used, it is preferred to provide a barrier coat such as silica. In the case of organic materials, materials excellent in heat resistance, dimensional stability, solvent resistance, electrical insulating properties and processability are preferably used.

The shape, structure and size of the substrate are not especially restricted, and these can be arbitrarily selected in accordance with the intended use and purpose of the luminescent device. In general, the substrate is preferably plate-shaped. The structure of the substrate may be a single layer structure or may be a lamination structure, and may consist of a single member or may be formed of two or more members.

The substrate may be colorless and transparent, or may be colored and transparent, but from the point of not scattering or attenuating the light emitted from the organic light-emitting layer, a colorless and transparent substrate is preferably used.

The substrate can be provided with a moisture permeation-preventing layer (a gas barrier layer) on the front surface or rear surface.

As the materials of the moisture permeation-preventing layer (the gas barrier layer), inorganic materials such as silicon nitride and silicon oxide are preferably used. The moisture permeation-preventing layer (the gas barrier layer) can be formed, for example, by a high frequency sputtering method.

When a thermoplastic substrate is used, if necessary, a hard coat layer and an undercoat layer may further be provided.

Anode:

The anode is generally sufficient to have the function of the electrode to supply holes to an organic layer. The shape, structure and size of the anode are not especially restricted, and these can be arbitrarily selected from known materials of electrode in accordance with the intended use and purpose of the luminescent device. The anode is generally provided as the transparent anode.

As the materials of anode, for example, metals, alloys, metallic oxides, electrically conductive compounds, and mixtures of these materials are preferably exemplified. The specific examples of the materials of anode include electrically conductive metallic oxides, e.g., tin oxides doped with antimony or fluorine (ATO, FTO), tin oxide, zinc oxide, indium oxide, indium tin oxide (ITO), indium zinc oxide (IZO), etc., metals, e.g., gold, silver, chromium, nickel, etc., mixtures or laminates of these metals with electrically conductive metallic oxides, inorganic electrically conductive substances, e.g., copper iodide, copper sulfide, etc., organic electrically conductive materials, e.g., polyaniline, polythiophene, polypyrrole, etc., laminates of these materials with ITO, etc. Of these materials, electrically conductive metallic oxides are preferred, and ITO is especially preferred in view of productivity, high conductivity, transparency and the like.

The anode can be formed on the substrate in accordance with various methods arbitrarily selected from, for example, wet methods, e.g., a printing method, a coating method, etc., physical methods, e.g., a vacuum deposition method, a sputtering method, an ion plating method, etc., and chemical methods, e.g., a CVD method, a plasma CVD method, etc., taking the suitability with the material to be used in the anode into consideration. For example, in the case of selecting ITO as the material of the anode, the anode can be formed according to a direct current or high frequency sputtering method, a vacuum deposition method, an ion plating method, etc.

In the organic electroluminescent device in the invention, the position of the anode to be formed is not especially restricted and can be formed anywhere in accordance with the intended use and purpose of the luminescent device, but preferably provided on the substrate. In this case, the anode may be formed on the entire surface of one side of the substrate, or may be formed at a part.

As patterning in forming the anode, patterning may be performed by chemical etching such as by photo-lithography, may be carried out by physical etching by laser and the like, may be performed by vacuum deposition or sputtering on a superposed mask, or a lift-off method and a printing method may be used.

The thickness of the anode can be optionally selected in accordance with the materials of the anode, so that it cannot be regulated unconditionally, but the thickness is generally from 10 nm to 50 µm or so, and is preferably from 50 nm to 20 µm.

The value of resistance of the anode is preferably $10^3 \Omega/\square$ or less, and more preferably $10^2 \Omega/\square$ or less. In the case where the anode is transparent, it may be colorless and transparent, or may be colored and transparent. For collecting emission from the transparent anode side, the transmittance is preferably 60% or more, and more preferably 70% or more.

In connection with transparent anodes, description is found in Yutaka Sawada supervised, *Tomei Denkyoku-Maku no Shintenkai* (*New Development in Transparent Conductive Films*), CMC Publishing Co., Ltd. (1999), and the description therein can be applied to the invention. In the case of using a plastic substrate low in heat resistance, a transparent anode film formed with ITO or IZO at a low temperature of 150° C. or less is preferred.

Cathode:

The cathode is generally sufficient to have the function of the electrode to inject electrons to organic layers. The shape, structure and size of the cathode are not especially restricted, and these can be arbitrarily selected from known materials of electrode in accordance with the intended use and purpose of the luminescent device.

As the materials to constitute the cathode, for example, metals, alloys, metallic oxides, electrically conductive compounds, and mixtures of these materials are exemplified. The specific examples of the materials of cathode include alkali metals (e.g., Li, Na, K, Cs, etc.), alkaline earth metals (e.g., Mg, Ca, etc.), gold, silver, lead, aluminum, sodium-potassium alloy, lithium-aluminum alloy, magnesium-silver alloy, indium, rare earth metals, e.g., ytterbium, etc. These materials may be used by one kind alone, but from the viewpoint of the compatibility of stability and an electron injecting property, two or more kinds of materials can be preferably used in combination.

As the materials constituting the cathode, alkali metals and alkaline earth metals are preferred of these materials in the point of an electron injecting property, and materials mainly comprising aluminum are preferred for their excellent preservation stability.

The materials mainly comprising aluminum mean aluminum alone, alloys of aluminum with 0.01 to 10 wt % of alkali metal or alkaline earth metal, or mixtures of these (e.g., lithium-aluminum alloy, magnesium-aluminum alloy, etc.).

The materials of the cathode are disclosed in detail in JP-A-2-15595 and JP-A-5-121172, and the materials described in these patents can also be used in the invention.

The cathode can be formed by known methods with no particular restriction. For example, the cathode can be formed according to wet methods, e.g., a printing method, a coating method, etc., physical methods, e.g., a vacuum deposition method, a sputtering method, an ion plating method, etc., and chemical methods, e.g., a CVD method, a plasma CVD method, etc., taking the suitability with the material constituting the cathode into consideration. For example, in the case of selecting metals as the materials of the cathode, the cathode can be formed with one or two or more kinds of the materials at the same time or in order by a sputtering method, etc.

Patterning in forming the cathode may be performed by chemical etching such as a method by photo-lithography, may be carried out by physical etching such as a method by laser, may be performed by vacuum deposition or sputtering on a superposed mask, or a lift-off method and a printing method may be used.

The position of the cathode to be formed is not especially restricted and can be formed anywhere in the invention. The cathode may be formed on the entire surface of the organic layer, or may be formed at a part.

A dielectric layer comprising fluoride or oxide of alkali metal or alkaline earth metal may be inserted between the cathode and the organic layer in a thickness of from 0.1 to 5 nm. The dielectric layer can be regarded as a kind of an electron-injecting layer. The dielectric layer can be formed, for example, according to a vacuum deposition method, a sputtering method, an ion plating method, etc.

The thickness of the cathode can be optionally selected in accordance with the materials of the cathode, so that it cannot be regulated unconditionally, but the thickness is generally from 10 nm to 5 µm or so, and is preferably from 50 nm to 1 µm.

The cathode may be transparent or opaque. The transparent cathode can be formed by forming a membrane of the material of the cathode in a thickness of from 1 to 10 nm, and further laminating transparent conductive materials such as ITO and IZO.

Organic Layer:

The organic layer in the invention is described below. The device in the invention has at least one organic layer including a light-emitting layer, and as organic layers other than the light-emitting layer, a hole-transporting layer, an electron-transporting layer, a hole-blocking layer, an electron-blocking layer, a hole-injecting layer, and an electron-injecting layer are exemplified, as described above.

Formation of Organic Layer:

In the organic electroluminescence device of the invention, each organic layer can be preferably formed by any of dry film-forming methods, e.g., a vacuum evaporation method and a sputtering method, a transfer method, a printing method, etc.

Light-Emitting Layer:

The light-emitting layer is a layer having functions to receive, at the time of electric field application, holes from the anode, hole-injecting layer or hole-transporting layer, and to receive electrons from the cathode, electron-injecting layer or electron-transporting layer, and offer the field of recombination of holes and electrons to emit light.

The light-emitting layer in the invention may consist of light-emitting materials alone, or may comprise a mixed layer of a host material and a light-emitting material. The light-emitting material may be a fluorescent material or may be a phosphorescent material, and a dopant may be one or two or more kinds. The host material is preferably a charge transporting material. The host material may be one or two or more kinds. For example, a constitution of a mixture of an electron-transporting host material and a hole-transporting host material is exemplified. Further, a material not having a charge-transporting property and not emitting light may be contained in the light-emitting layer. As the light-emitting layer, a light-emitting layer using the complex of the invention as the light-emitting material and the host material is preferred.

The light-emitting layer may be a single layer, or may comprise two or more layers, and each layer may emit light in different luminescent colon The examples of fluorescent materials capable of being used in the invention include various complexes represented by complexes of benzoxazole derivatives, benzimidazole derivatives, benzothiazole derivatives, styrylbenzene derivatives, polyphenyl derivatives, diphenylbutadiene derivatives, tetraphenylbutadiene derivatives, naphthalimide derivatives, coumarin derivatives, condensed aromatic compounds, perinone derivatives, oxadiazole derivatives, oxazine derivatives, aldazine derivatives, pyraridine derivatives, cyclopentadiene derivatives, bisstyrylanthracene derivatives, quinacridone derivatives, pyrrolopyridine derivatives, thiadiazolopyridine derivatives, cyclopentadiene derivatives, styrylamine derivatives, diketopyrrolopyrrole derivatives, aromatic dimethylidyne compounds, 8-quinolinol derivatives and complexes of pyromethene derivatives, polymer compounds such as polythiophene, polyphenylene, polyphenylenevinylene, etc., and compounds such as organic silane derivatives.

As the phosphorescent materials usable in the invention, in addition to the compounds of the invention, phosphorescent compounds disclosed, for example, in U.S. Pat. Nos. 6,303,238B1, 6,097,147, WO 00/57,676, WO 00/70,655, WO 01/08,230, WO 01/39,234A2, WO 01/41,512A1, WO 02/02,714A2, WO 02/15,645A1, WO 02/44,189A1, WO 05/19,373A2, JP-A-2001-247859, JP-A-2002-302671, JP-A-2002-117978, JP-A-2003-133074, JP-A-2002-235076, JP-A-2003-123982, JP-A-2002-170684, EP 1,211, 257, JP-A-2002-226495, JP-A-2002-234894, JP-A-2001-247859, JP-A-2001-298470, JP-A-2002-173674, JP-A-2002-203678, JP-A-2002-203679, JP-A-2004-357791, JP-A-2006-256999, JP-A-2007-19462, JP-A-2007-84635, and JP-A-2007-96259 are exemplified. As further preferred light-emitting dopants, an Ir complex, a Pt complex, a Cu complex, an Re complex, a W complex, an Rh complex, an Ru complex, a Pd complex, an Os complex, an Eu complex, a Tb complex, a Gd complex, a Dy complex, and a Ce complex are exemplified. As especially preferred dopants, an Ir complex, a Pt complex and an Re complex are exemplified. An Ir complex, a Pt complex and an Re complex including at least one coordination system of a metal-carbon bond, a metal-nitrogen bond, a metal-oxygen bond, and a metal-sulfur bond are preferred above all. Further, from the aspects of luminous efficiency, driving durability and chromaticity, an Ir complex, a Pt complex and an Re complex containing a tridentate or higher multidentate ligand are especially preferred.

The content of phosphorescent materials in a light-emitting layer is preferably in the range of 0.1 wt % or more and 50 wt % or less of the total mass of the light-emitting layer, more preferably in the range of 0.2 wt % or more and 50 wt % or less, still more preferably in the range of 0.3 wt % or more and 40 wt % or less, and most preferably in the range of 20 wt % or more and 30 wt % or less.

The thickness of a light-emitting layer is not especially restricted, and generally preferably from 1 to 500 nm, more preferably from 5 to 200 nm, and still more preferably from 10 to 100 nm.

Hole Injecting Layer and Hole Transporting Layer:

The hole-injecting layer and the hole-transporting layer are layers having the functions of receiving holes from the anode or anode side and transporting the holes to the cathode side. The hole-injecting layer and the hole-transporting layer are preferably layers specifically containing carbazole derivatives, triazole derivatives, oxazole derivatives, oxadiazole derivatives, imidazole derivatives, polyarylalkane derivatives, pyrazoline derivatives, pyrazolone derivatives, phenylenediamine derivatives, arylamine derivatives, amino-substituted chalcone derivatives, styrylanthracene derivatives, fluorenone derivatives, hydrazone derivatives, stilbene derivatives, silazane derivatives, aromatic tertiary amine compounds, styrylamine compounds, porphyrin compounds, organic silane derivatives, or carbon.

The thickness of the hole-injecting layer and hole transporting layer is each preferably 500 nm or less in view of lowering driving voltage.

The thickness of the hole-transporting layer is preferably from 1 to 500 nm, more preferably from 5 to 200 nm, and still more preferably from 10 to 100 nm. The thickness of the hole-injecting layer is preferably from 0.1 to 200 nm, more preferably from 0.5 to 100 nm, and still more preferably from 1 to 100 nm.

The hole-injecting layer and the hole-transporting layer may have a single layer structure comprising one kind or two or more kinds of the above materials, or may be a multilayer structure comprising a plurality of layers having the same composition or different compositions.

Electron Injecting Layer and Electron Transporting Layer:

The electron-injecting layer and the electron-transporting layer are layers having functions of receiving electrons from the cathode or cathode side and transporting the electrons to the anode side.

The electron-injecting layer and the electron-transporting layer are specifically preferably layers containing various complexes represented by complexes of triazole derivatives, oxazole derivatives, oxadiazole derivatives, imidazole derivatives, fluorenone derivatives, anthraquinodimethane derivatives, anthrone derivatives, diphenylquinone derivatives, thiopyran dioxide derivatives, carbodiimide derivatives, fluorenylidenemethane derivatives, distyrylpyrazine derivatives, aromatic cyclic tetracarboxylic anhydrides such as naphthalene and perylene, phthalocyanine derivatives, complexes of 8-quinolinol derivatives, complexes having metalphthalocyanine, benzoxazole or benzothiazole as the ligand, and organic silane derivatives.

The thickness of the electron injecting layer and the electron transporting layer is preferably 500 nm or less from the point of lowering the driving voltage.

The thickness of the electron transporting layer is preferably from 1 to 500 nm, more preferably from 5 to 200 nm, and still more preferably from 10 to 100 nm. The thickness of the electron injecting layer is preferably from 0.1 to 200 nm, more preferably from 0.2 to 100 nm, and still more preferably from 0.5 to 50 nm.

The electron injecting layer and the electron transporting layer may have a single layer structure comprising one kind or two or more kinds of the above materials, or may be a multilayer structure comprising a plurality of layers having the same composition or different compositions.

Hole-Blocking Layer:

The hole-blocking layer is a layer having a function of preventing the holes transported from the anode side to the light-emitting layer from passing through to the cathode side. In the invention, a hole-blocking layer can be provided as an organic layer contiguous to the light-emitting layer on the cathode side.

As the examples of the organic compounds constituting the hole-blocking layer, aluminum complexes such as aluminum(III)bis(2-methyl-8-quinolinato)-4-phenylphenolate (abbreviation: BAlq), triazole derivatives, and phenanthroline derivatives such as 2,9-dimethyl-4,7-diphenyl-1,10-phenanthroline (abbreviation: BCP) can be exemplified.

The thickness of the hole-blocking layer is preferably from 1 to 500 nm, more preferably from 5 to 200 nm, and still more preferably from 10 to 100 nm.

The hole-blocking layer may have a single layer structure comprising one kind or two or more kinds of the above materials, or may be a multilayer structure comprising a plurality of layers having the same composition or different compositions.

Protective Layer:

In the invention, the organic EL device may be entirely protected with a protective layer.

The materials contained in the protective layer are sufficient to have a function of preventing substances that accelerate deterioration of the device such as water and oxygen from entering the device.

As the examples of the materials, metals, e.g., In, Sn, Pb, Au, Cu, Ag, Al, Ti, Ni, etc., metallic oxides, e.g., MgO, SiO, $SiO_2$, $Al_2O_3$, GeO, NiO, CaO, BaO, $Fe_2O_3$, $Y_2O_3$, $TiO_2$, etc., metallic nitrides, e.g., $SiN_x$, $SiN_xO_y$, etc., metallic fluorides, e.g., $MgF_2$, LiF, $AlF_3$, $CaF_2$, etc., copolymers of any of polyethylene, polypropylene, polymethyl methacrylate, polyimide, polyurea, polytetrafluoroethylene, polychlorotrifluoroethylene, polydichlorodifluoroethylene, and chlorotrifluoroethylene with dichlorodifluoroethylene, copolymers obtained by copolymerization of tetrafluoroethylene and monomer mixture containing at least one kind of comonomer, fluorine-containing copolymers having a cyclic structure in the copolymer main chain, water-absorbing materials having a coefficient of water absorption of 1% or more, and moisture-proof materials having a coefficient of water absorption of 0.1% or less are exemplified.

The method of forming the protective layer is not especially restricted and, for example, a vacuum deposition method, a sputtering method, a reactive sputtering method, an MBE (molecular beam epitaxy) method, a cluster ion beam method, an ion plating method, a plasma polymerization method (a high frequency excitation ion plating method), a plasma CVD method, a laser CVD method, a thermal CVD method, a gas source CVD method, a coating method, a printing method, and a transfer method can be used.

Sealing Case:

The device in the invention may be entirely sealed with a sealing case.

A water-absorbing agent or an inactive liquid may be sealed in the space between the sealing case and the device. The water-absorbing agent is not especially restricted, and, for example, barium oxide, sodium oxide, potassium oxide, calcium oxide, sodium sulfate, calcium sulfate, magnesium sulfate, phosphorus pentoxide, calcium chloride, magnesium chloride, copper chloride, cesium fluoride, niobium fluoride, calcium bromide, vanadium bromide, molecular sieve, zeolite, and magnesium oxide can be exemplified. The inactive liquid is not especially restricted, and, for example, paraffins, liquid paraffins, fluorine solvents, e.g., perfluoroalkane, perfluoroamine, perfluoroether, etc., chlorine solvents, and silicone oils can be exemplified.

By the application of D.C. (if necessary, A.C. component may be contained) voltage (generally from 2 to 15 volts) between the anode and the cathode, or by the application of D.C. electric current, light emission of the device of the invention can be obtained.

With respect to the driving method of the device of the invention, the driving methods disclosed in JP-A-2-148687, JP-A-6-301355, JP-A-5-29080, JP-A-7-134558, JP-A-8-234685, JP-A-8-241047, Japanese Patent 2784615, U.S. Pat. Nos. 5,828,429 and 6,023,308 can be applied to the invention.

The device in the invention can be preferably used in display devices, displays, backlights, electrophotography, illumination light sources, recording light sources, exposure light sources, reading light sources, indicators, signboards, interior designs, optical communications, and the like.

EXAMPLE

The invention will be described more specifically with reference to examples, but the scope of the invention is by no means restricted thereto.

Synthesis of Exemplified Compound 32

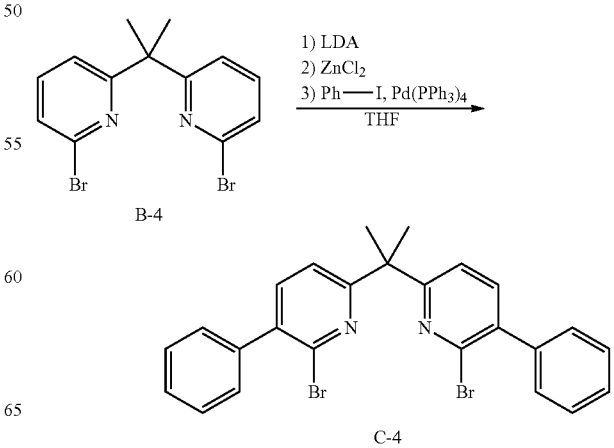

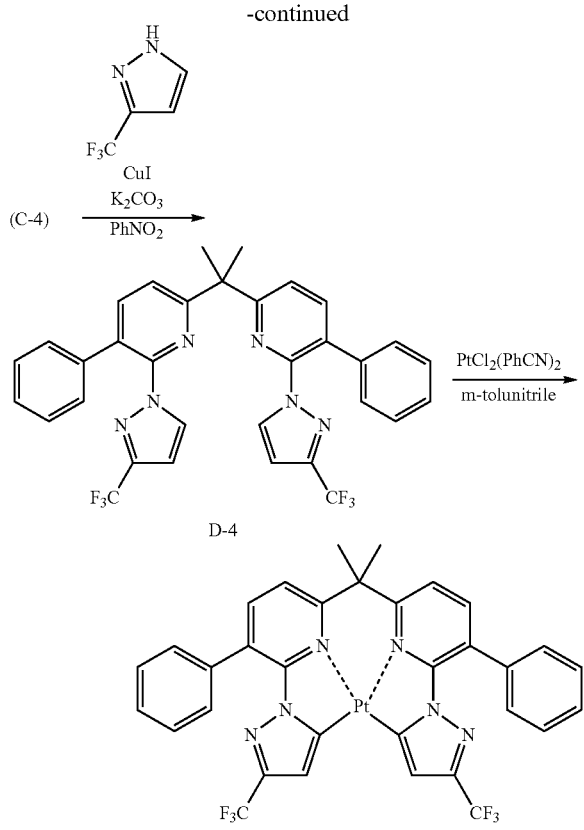

Synthesis of Compound (C-4)

Under nitrogen atmosphere, Compound (B-4) (35.60 g, 100 mmol), and 300 ml of tetrahydrofuran are put in a three-neck flask, and the mixture is cooled to −70° C. or lower with a dry ice-acetone bath. After 120 ml of a 1.8 M lithium diisopropyl-amide (LDA)-heptane•tetrahydrofuran•ethylbenzene solution is dripped to the above reaction mixture, zinc chloride (II) (32.00 g, 230 mmol)-tetrahydrofuran (200 mmol) is dripped to the mixture, the temperature is raised up to room temperature, and the reaction mixture is stirred for 1 hour. Subsequently, iodobenzene (61.0 g, 300 mmol) and tetrakis(triphenylphosphine) palladium (O) (11.55 g, 10 mmol) are added to the reaction solution, followed by heat-refluxing while staring for 24 hours. After the temperature is lowered to room temperature, an organic layer obtained by extraction with ethyl acetate is dried with magnesium sulfate, filtered, and concentrated. The obtained residue is refined by silica gel column chromatography (toluene/hexane: 1/1), and 8.4 g of Compound (C-4) is obtained as white crystal (yield: 14.4%).

$^1$H-NMR (CDCl$_3$) 300 MHz δ: 1.87 (s, 6H), 7.29 (d, j=6.0 Hz, 2H), 7.40-7.45 (m, 10H), 7.53 (d, J=5.7 Hz, 2H)

Synthesis of Compound (D-4)

Under nitrogen atmosphere, Compound (C-4) (3.56 g, 7.0 mmol), 3-(trifluoromethyl)pyrazole (2.61 g, 28 mmol), copper iodide (0.27 g, 1.4 mmol), potassium carbonate (5.81 g, 42 mmol), and 140 ml of nitrobenzene are put in a three-neck flask, and the mixture is heat-refluxed while stirring for 12 hours. After the temperature is lowered to room temperature, an organic layer obtained by extraction with ethyl acetate is dried with sodium sulfate, filtered, and concentrated. The obtained residue is refined by silica gel column chromatography (hexane/ethyl acetate: 4/1), and 331 g of Compound (D-4) is obtained as white crystal (yield: 88.5%).

$^1$H-NMR (CDCl$_3$) 300 MHz δ: 1.93 (s, 6H), 6.57 (d, J=2.7 Hz, 2H), 7.05-7.09 (m, 4H), 7.28-7.32 (m, 6H), 8.43 (d, J=7.8 Hz, 2H), 7.92 (d, J=0.9 Hz, 2H)

Synthesis of Exemplified Compound 32

Under nitrogen atmosphere, Compound (D-4) (3.4 g, 5.5 mmol), platinous chloride benzonitrile complex (2.60 g, 5.5 mmol), and 100 ml of m-tolunitrile are put in an eggplant type flask, and the mixture is heat-refluxed while stirring for 5 hours. After the temperature is lowered to room temperature, 150 ml of methanol is added thereto, precipitated solid recovered by filtration is dried under reduced pressure to obtain 3.7 g of Exemplified Compound 32 as yellow crystal (yield: 82.9%). λmax=464 nm (a dichloromethane solution).

$^1$H-NMR (CDCl$_3$) 300 MHz δ: 2.14 (s, 6H), 6.57 (t, J (Pt—H)=8.5 Hz, 2H), 7.26-7.38 (m, 4H), 7.40-7.41 (m, 6H), 7.57 (d, J=8.4 Hz, 2H), 7.92 (d, J=8.1 Hz, 2H)

Synthesis of Exemplified Compound 47

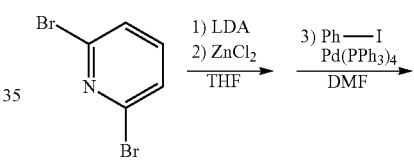

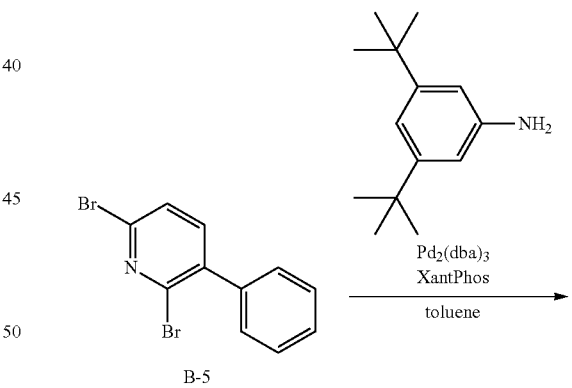

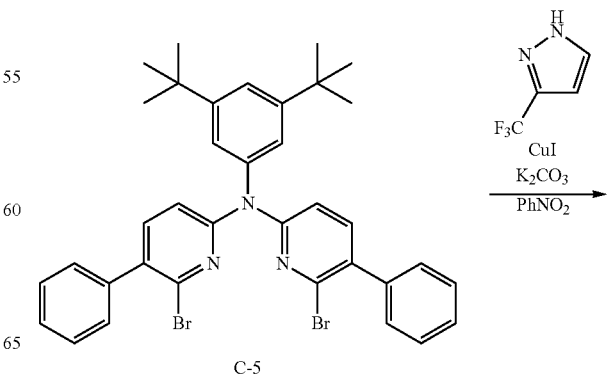

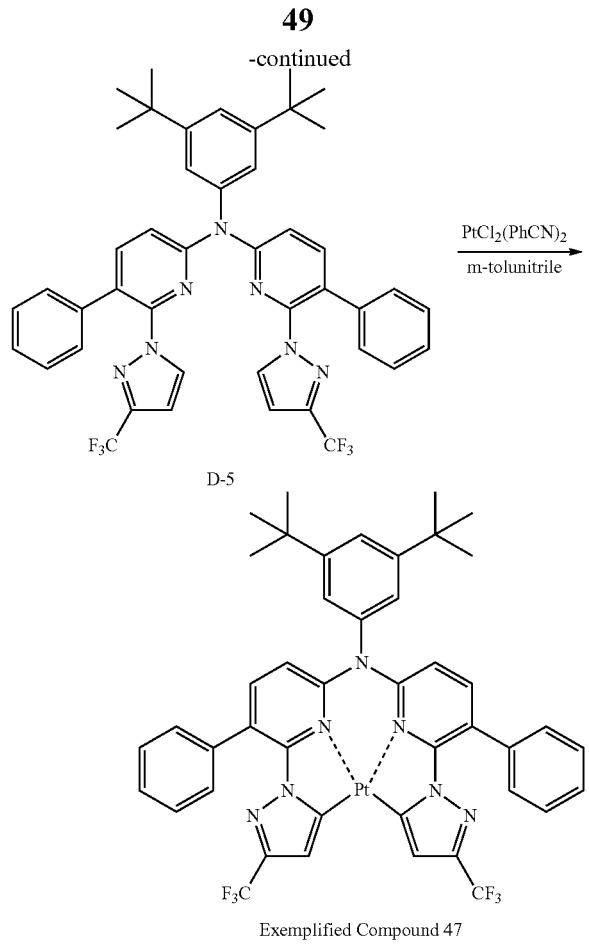

Exemplified Compound 47

Synthesis of Compound (B-5)

Under nitrogen atmosphere, 2,6-dibromopyridine (23.68 g, 100 mmol), and 200 ml of tetrahydrofuran are put in a three-neck flask, and the mixture is cooled to −70° C. or lower with a dry ice-acetone bath. After 60 ml of a 1.8 M lithium diisopropylamide (LDA)-heptane•tetrahydrofuran•ethylbenzene solution is dripped to the above reaction mixture, zinc chloride (II) (13.63 g, 100 mmol)-tetrahydrofuran (100 mmol) is dripped to the mixture, the temperature is raised up to room temperature, and the reaction mixture is stirred for 1 hour. Subsequently, iodobenzene (40.8 g, 200 mmol) and tetrakis(triphenylphosphine) palladium (O) (5.8 g, 5 mmol) are added to the reaction solution, followed by heat-refluxing while stirring for 24 hours. After the temperature is lowered to room temperature, an organic layer obtained by extraction with ethyl acetate is dried with magnesium sulfate, filtered, and concentrated. The obtained residue is refined by silica gel column chromatography (ethyl acetate/hexane: 1/20), and 11.9 g of Compound (B-5) is obtained as transparent oil (yield: 37.9%).

$^1$H-NMR (CDCl$_3$) 300 MHz δ: 7.48-752 (m, 3H), 7.58-7.60 (m, 2H), 7.67-7.68 (m, 2H)

Synthesis of Compound (C-5)

Under nitrogen atmosphere, Compound (B-5) (5.60 g, 17.8 mmol), 3,5-di-tert-butylaniline (1.23 g, 6.0 mmol), tris(dibenzylideneacetone)dipalladium (O) (0.27 g, 0.3 mmol), 4,5-bis(diphenylphosphino)-9,9-dimethylxanthene (XantPhos) (0.34 g, 0.6 mmol), sodium tert-butoxy (1.92 g, 20 mmol), and 60 ml of toluene are put in a three-neck flask, and the mixture is heat-refluxed while stirring for 12 hours. After the temperature is lowered to room temperature, an organic layer obtained by extraction with ethyl acetate is dried with sodium sulfate, filtered, and concentrated. The obtained residue is refined by silica gel column chromatography (hexane/ethyl acetate: 4/1), and 3.81 g of Compound (C-5) is obtained as red oil (yield: 95.0%).

Synthesis of Compound (D-5)

Under nitrogen atmosphere, Compound (C-5) (3.68 g, 5.5 mmol), 3-(trifluoromethyl)pyrazole (2.04 g, 22 mmol), copper iodide (0.27 g, 1.4 mmol), potassium carbonate (5.81 g, 42 mmol), and 120 ml of nitrobenzene are put in a three-neck flask, and the mixture is heat-refluxed while stirring for 12 hours. After the temperature is lowered to room temperature, an organic layer obtained by extraction with ethyl acetate is dried with sodium sulfate, filtered, and concentrated. The obtained residue is refined by silica gel column chromatography (hexane/ethyl acetate: 4/1), and 1.35 g of Compound (D-5) is obtained as white crystal (yield: 28.8%).

$^1$H-NMR (CDCl$_3$) 300 MHz δ: 1.32 (s, 18H), 6.58 (d, J=2.7 Hz, 2H), 7.21 (d, J=1.8 Hz, 2H), 7.41-7.46 (m, 8H), 7.60-7.63 (m, 4H), 7.91 (d, 3=1.2 Hz, 2H), 8.21 (d, J=1.5 Hz, 2H)

Synthesis of Exemplified Compound 47

Under nitrogen atmosphere, Compound (D-5) (1.1 g, 1.4 mmol), platinous chloride benzonitrile complex (0.66 g, 1.4 mmol), and 30 ml of m-tolunitrile are put in an eggplant type flask, and the mixture is heat-refluxed while stirring for 6 hours. After the temperature is lowered to room temperature, 50 ml of methanol is added thereto, precipitated solid recovered by filtration is dried under reduced pressure to obtain 1.13 g of Exemplified Compound 47 as yellow crystal (yield: 83.0%). λmax=462 nm (a dichloromethane solution).

$^1$H-NMR (CDCl$_3$) 300 MHz δ: 1.42 (s, 18H), 6.73 (t, J (Pt—H)=7.2 Hz, 2H), 7.39-7.47 (m, 15H), 7.90 (d, J=1.5 Hz, 2H)

Comparative Example 1

An ITO substrate (a glass substrate having an ITO film (manufactured by Geomatec Co., Ltd., surface resistance: 10Ω/□)) having a size of 2.5 cm square and a thickness of 0.5 mm is put in a washer and subjected to ultrasonic washing in 2-propanol, and then UV-ozone treatment for 30 minutes to be cleaned. The ITO substrate is placed in a vacuum evaporator, copper phthalocyanine is deposited on the substrate in a thickness of 10 nm, and NPD (N,N'-di-α-naphthyl-N,N'-diphenyl)-benzidine is deposited thereon in a thickness of 40 nm. mCP and the Compound 2 disclosed in JP-A-2007-19462 in a ratio of 80/20 (by mass) are deposited on the above deposited film in a thickness of 10 nm, then BAlq is deposited thereon in a thickness of 40 nm, and then lithium fluoride is deposited thereon in a thickness of 3 nm, followed by deposition of aluminum in a thickness of 60 nm to prepare a device. The obtained EL device is subjected to application of DC constant voltage with a source measure unit Model 2400 (manufactured by Toyo Corporation) to emit light. It is confirmed that the emission of blue light originating in Compound 2 described in JP-A-2007-19462 is obtained.

The chemical structures of the above copper phthalocyanine, NPD, Compound 2 described in JP-A-2007-19462, mCP and BAlq are shown below.
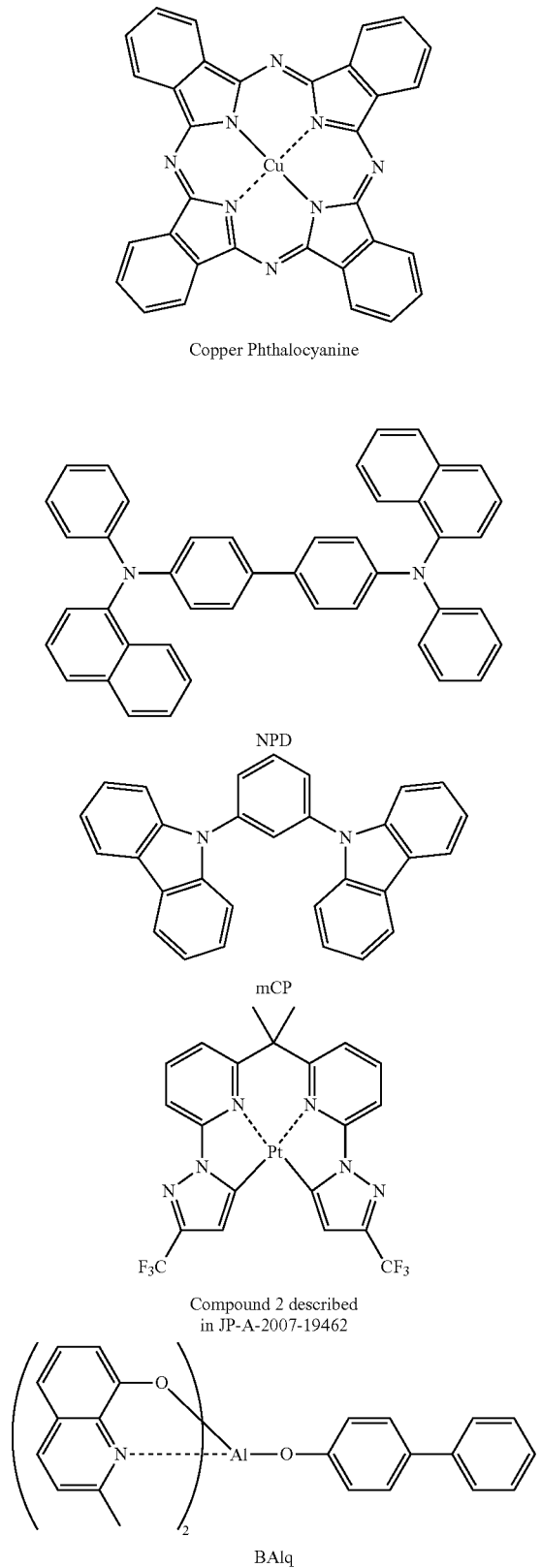
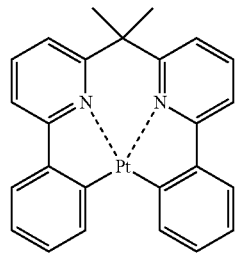
Compound 79 described
in JP-A-2005-310733
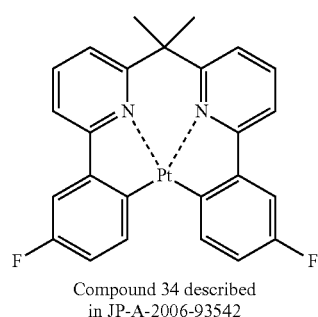
Compound 34 described
in JP-A-2006-93542
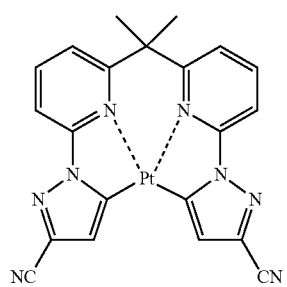
Compound 5 described
in JP-A-2007-19462
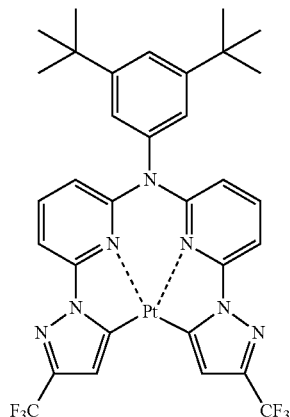
Compound 255 described
in JP-A-2007-19462

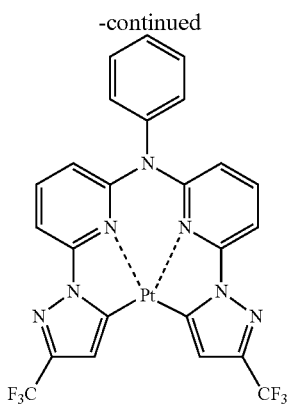

Compound 249 described in JP-A-2007-19462

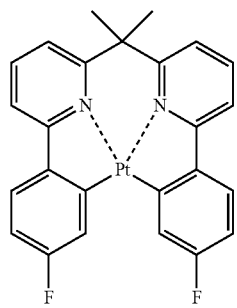

Comparative Compound 1

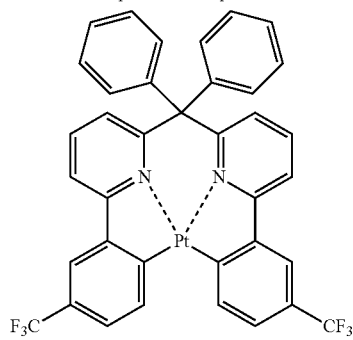

Comparative Compound 2

Comparative Example 2

An organic EL device in Comparative Example 2 is manufactured in the same manner as in Comparative Example 1 except for changing the ratio of mCP and Compound 2 described in JP-A-2007-19462 to 70/30. The obtained EL device is subjected to application of DC constant voltage with a source measure unit Model 2400 (manufactured by Toyo Corporation) to emit light. It is confirmed that the emission of blue light originating in Compound 2 described in JP-A-2007-19462 is obtained.

Example 1

An organic EL device in Example 1 is manufactured in the same manner as in Comparative Example 1 except for using Exemplified Compound 32 according to the invention in place of Compound 2 described in JP-A-2007-19462. The obtained EL device is subjected to application of DC constant voltage with a source measure unit Model 2400 (manufactured by Toyo Corporation) to emit light. It is confirmed that the emission of blue light originating in Exemplified Compound 32 of the invention is obtained.

Example 2

An organic EL device in Example 2 is manufactured in the same manner as in Example 1 except for changing the ratio of mCP and Exemplified Compound 32 of the invention to 70/30. The obtained EL device is subjected to application of DC constant voltage with a source measure unit Model 2400 (manufactured by Toyo Corporation) to emit light. It is confirmed that the emission of blue light originating in Exemplified Compound 32 of the invention is obtained.

Evaluation of Luminescence Device:

Each of luminescence devices obtained is driven by constant current at 20° C., and luminance is measured with a luminometer BM-8 (a trade name, manufactured by Topcon Corporation). Change in chromaticity is computed from emission spectrum measured at 20° C. (CIE chromaticity value (xy chromaticity value) found with a light emission spectrum measuring system (ELS1500), manufactured by Shimadzu Corporation).

Relative luminance and CIE chromaticity of each of devices manufactured are shown in Table 1 below. From Table 1, it can be seen that the compound of the invention is little in chromaticity variation of light emission due to addition concentration even when the compound is added in high concentration.

TABLE 1

| | Addition Concentration of Phosphorescent Material (%) | Relative Luminance at the Time of Application of 12 V | CIE Chromaticity |
|---|---|---|---|
| Comparative Example 1 | 20 | 100 | (0.19, 0.30) |
| Comparative Example 2 | 30 | 110 | (0.25, 0.33) |
| Example 1 | 20 | 98 | (0.17, 0.29) |
| Example 2 | 30 | 113 | (0.18, 0.30) |

Comparative Example 3

An organic EL device in Comparative Example 3 is manufactured in the same manner as in Comparative Example 1 except for using Compound 79 described in JP-A-2005-310733 in place of Compound 2 described in JP-A-2007-19462. The obtained EL device is subjected to application of DC constant voltage with a source measure unit Model 2400 (manufactured by Toyo Corporation) to emit light. It is confirmed that the emission of green light originating in Compound 79 in JP-A-2005-310733 is obtained.

Comparative Example 4

An organic EL device in Comparative Example 4 is manufactured in the same manner as in Comparative Example 3 except for changing the ratio of mCP and Compound 79 described in JP-A-2005-310733 to 70/30. The obtained EL device is subjected to application of DC constant voltage with a source measure unit Model 2400 (manufactured by Toyo Corporation) to emit light. It is confirmed that the emission of green light originating in Compound 79 described in JP-A-2005-310733 is obtained.

Example 3

An organic EL device in Example 3 is manufactured in the same manner as in Comparative Example 1 except for using Exemplified Compound 1 according to the invention in place of Compound 2 described in JP-A-2007-19462. The obtained EL device is subjected to application of DC constant voltage with a source measure unit Model 2400 (manufactured by Toyo Corporation) to emit light. It is confirmed that the emission of green light originating in Exemplified Compound 1 of the invention is obtained.

Example 4

An organic EL device in Example 4 is manufactured in the same manner as in Example 3 except for changing the ratio of mCP and Exemplified Compound 1 of the invention to 70/30. The obtained EL device is subjected to application of DC constant voltage with a source measure unit Model 2400 (manufactured by Toyo Corporation) to emit light. It is confirmed that the emission of green light originating in Exemplified Compound 1 of the invention is obtained.

Relative luminance and CIE chromaticity of each of devices manufactured are shown in Table 2 below. From Table 2, it can be seen that the compound of the invention is little in chromaticity variation of light emission due to addition concentration even when the compound is added in high concentration.

TABLE 2

| | Addition Concentration of Phosphorescent Material (%) | Relative Luminance at the Time of Application of 12 V | CIE Chromaticity |
|---|---|---|---|
| Comparative Example 3 | 20 | 100 | (0.30, 0.65) |
| Comparative Example 4 | 30 | 105 | (0.35, 0.63) |
| Example 3 | 20 | 102 | (0.29, 0.65) |
| Example 4 | 30 | 108 | (0.29, 0.64) |

Comparative Example 5

An organic EL device in Comparative Example 5 is manufactured in the same manner as in Comparative Example 1 except for using Compound 34 described in JP-A-2006-93542 in place of Compound 2 described in JP-A-2007-19462. The obtained EL device is subjected to application of DC constant voltage with a source measure unit Model 2400 (manufactured by Toyo Corporation) to emit light. It is confirmed that the emission of green light originating in Compound 34 described in JP-A-2006-93542 is obtained.

Comparative Example 6

An organic EL device in Comparative Example 6 is manufactured in the same manner as in Comparative Example 5 except for changing the ratio of mCP and Compound 34 described in JP-A-2006-93542 to 70/30. The obtained EL device is subjected to application of DC constant voltage with a source measure unit Model 2400 (manufactured by Toyo Corporation) to emit light. It is confirmed that the emission of green light originating in Compound 34 described in JP-A-2006-93542 is obtained.

Example 5

An organic EL device in Example 5 is manufactured in the same manner as in Comparative Example 1 except for using Exemplified Compound 4 according to the invention in place of Compound 2 described in JP-A-2007-19462. The obtained EL device is subjected to application of DC constant voltage with a source measure unit Model 2400 (manufactured by Toyo Corporation) to emit light. It is confirmed that the emission of green light originating in Exemplified Compound 4 according to the invention is obtained.

Example 6

An organic EL device in Example 6 is manufactured in the same manner as in Example 5 except for changing the ratio of mCP and Exemplified Compound 4 of the invention to 70/30. The obtained EL device is subjected to application of DC constant voltage with a source measure unit Model 2400 (manufactured by Toyo Corporation) to emit light. It is confirmed that the emission of green light originating in Exemplified Compound 4 of the invention is obtained.

Relative luminance and CIE chromaticity of each of devices manufactured are shown in Table 3 below. From Table 3, it can be seen that the compound of the invention is little in chromaticity variation of light emission due to addition concentration even when the compound is added in high concentration.

TABLE 3

| | Addition Concentration of Phosphorescent Material (%) | Relative Luminance at the Time of Application of 12 V | CIE Chromaticity |
|---|---|---|---|
| Comparative Example 5 | 20 | 100 | (0.31, 0.65) |
| Comparative Example 6 | 30 | 114 | (0.37, 0.62) |
| Example 5 | 20 | 106 | (0.30, 0.65) |
| Example 6 | 30 | 124 | (0.32, 0.64) |

Comparative Example 7

An organic EL device in Comparative Example 7 is manufactured in the same manner as in Comparative Example 1 except for using Compound 5 described in JP-A-2007-19462 in place of Compound 2 described in JP-A-2007-19462. The obtained EL device is subjected to application of DC constant voltage with a source measure unit Model 2400 (manufactured by Toyo Corporation) to emit light. It is confirmed that the emission of blue light originating in Compound 5 described in JP-A-2007-19462 is obtained.

Comparative Example 8

An organic EL device in Comparative Example 8 is manufactured in the same manner as in Comparative Example 7 except for changing the ratio of mCP and Compound 5 described in JP-A-2007-19462 to 70/30. The obtained EL device is subjected to application of DC constant voltage with a source measure unit Model 2400 (manufactured by Toyo Corporation) to emit light. It is confirmed that the emission of blue light originating in Compound 5 described in JP-A-2007-19462 is obtained.

Example 7

An organic EL device in Example 7 is manufactured in the same manner as in Comparative Example 1 except for using Exemplified Compound 33 according to the invention in place of Compound 2 described in JP-A-2007-19462. The obtained EL device is subjected to application of DC constant voltage with a source measure unit Model 2400 (manufactured by Toyo Corporation) to emit light. It is confirmed that the emission of blue light originating in Exemplified Compound 33 according to the invention is obtained.

Example 8

An organic EL device in Example 8 is manufactured in the same manner as in Example 7 except for changing the ratio of mCP and Exemplified Compound 33 of the invention to 70/30. The obtained EL device is subjected to application of DC constant voltage with a source measure unit Model 2400 (manufactured by Toyo Corporation) to emit light. It is confirmed that the emission of blue light originating in Exemplified Compound 33 of the invention is obtained.

Relative luminance and CIE chromaticity of each of devices manufactured are shown in Table 4 below. From Table 4, it can be seen that the compound of the invention is little in chromaticity variation of light emission due to addition concentration even when the compound is added in high concentration.

TABLE 4

| | Addition Concentration of Phosphorescent Material (%) | Relative Luminance at the Time of Application of 12 V | CIE Chromaticity |
|---|---|---|---|
| Comparative Example 7 | 20 | 100 | (0.17, 026) |
| Comparative Example 8 | 30 | 95 | (0.20, 0.31) |
| Example 7 | 20 | 105 | (0.17, 0.27) |
| Example 8 | 30 | 116 | (0.18, 0.29) |

Comparative Example 9

An organic EL device in Comparative Example 9 is manufactured in the same manner as in Comparative Example 1 except for using Compound 255 described in JP-A-2007-19462 in place of Compound 2 described in JP-A-2007-19462. The obtained EL device is subjected to application of DC constant voltage with a source measure unit Model 2400 (manufactured by Toyo Corporation) to emit light. It is confirmed that the emission of blue light originating in Compound 255 described in JP-A-2007-19462 is obtained.

Comparative Example 10

An organic EL device in Comparative Example 10 is manufactured in the same manner as in Comparative Example 9 except for changing the ratio of mCP and Compound 255 described in JP-A-2007-19462 to 70/30. The obtained EL device is subjected to application of DC constant voltage with a source measure unit Model 2400 (manufactured by Toyo Corporation) to emit light. It is confirmed that the emission of blue light originating in Compound 255 described in JP-A-2007-19462 is obtained.

Example 9

An organic EL device in Example 9 is manufactured in the same manner as in Comparative Example 1 except for using Exemplified Compound 47 according to the invention in place of Compound 2 described in JP-A-2007-19462. The obtained EL device is subjected to application of DC constant voltage with a source measure unit Model 2400 (manufactured by Toyo Corporation) to emit light. It is confirmed that the emission of blue light originating in Exemplified Compound 47 according to the invention is obtained.

Example 10

An organic EL device in Example 10 is manufactured in the same manner as in Example 9 except for changing the ratio of mCP and Exemplified Compound 47 according to the invention to 70/30. The obtained EL device is subjected to application of DC constant voltage with a source measure unit Model 2400 (manufactured by Toyo Corporation) to emit light. It is confirmed that the emission of blue light originating in Exemplified Compound 47 according to the invention is obtained.

Relative luminance and CIE chromaticity of each of devices manufactured are shown in Table 5 below. From Table 5, it can be seen that the compound of the invention is little in chromaticity variation of light emission due to addition concentration even when the compound is added in high concentration.

TABLE 5

| | Addition Concentration of Phosphorescent Material (%) | Relative Luminance at the Time of Application of 12 V | CIE Chromaticity |
|---|---|---|---|
| Comparative Example 9 | 20 | 100 | (0.20, 0.29) |
| Comparative Example 10 | 30 | 104 | (0.23, 0.35) |
| Example 9 | 20 | 102 | (0.20, 0.28) |
| Example 10 | 30 | 110 | (0.21, 0.31) |

Comparative Example 11

An organic EL device in Comparative Example 11 is manufactured in the same manner as in Comparative Example 1 except for using Compound 249 described in JP-A-2007-19462 in place of Compound 2 described in JP-A-2007-19462. The obtained EL device is subjected to application of DC constant voltage with a source measure unit Model 2400 (manufactured by Toyo Corporation) to emit light. It is confirmed that the emission of blue light originating in Compound 249 described in JP-A-2007-19462 is obtained.

Comparative Example 12

An organic EL device in Comparative Example 12 is manufactured in the same manner as in Comparative Example 11 except for changing the ratio of mCP and Compound 249 described in JP-A-2007-19462 to 70/30. The obtained EL device is subjected to application of DC constant voltage with a source measure unit Model 2400 (manufactured by Toyo Corporation) to emit light. It is confirmed that the emission of blue light originating in Compound 249 described in JP-A-2007-19462 is obtained.

Example 11

An organic EL device in Example 11 is manufactured in the same manner as in Comparative Example 1 except for using Exemplified Compound 69 according to the invention in place of Compound 2 described in JP-A-2007-19462. The obtained EL device is subjected to application of DC constant voltage with a source measure unit Model 2400 (manufactured by Toyo Corporation) to emit light. It is confirmed that the emission of blue light originating in Exemplified Compound 69 according to the invention is obtained.

Example 12

An organic EL device in Example 12 is manufactured in the same manner as in Example 11 except for changing the ratio of mCP and Exemplified Compound 69 according to the invention to 70/30. The obtained EL device is subjected to application of DC constant voltage with a source measure unit Model 2400 (manufactured by Toyo Corporation) to emit light. It is confirmed that the emission of blue light originating in Exemplified Compound 69 according to the invention is obtained.

Relative luminance and CIF, chromaticity of each of devices manufactured are shown in Table 6 below. From Table 6, it can be seen that the compound of the invention is little in chromaticity variation of light emission due to addition concentration even when the compound is added in high concentration.

TABLE 6

|  | Addition Concentration of Phosphorescent Material (%) | Relative Luminance at the Time of Application of 12 V | CIE Chromaticity |
|---|---|---|---|
| Comparative Example 11 | 20 | 100 | (0.19, 0.28) |
| Comparative Example 12 | 30 | 105 | (0.23, 0.33) |
| Example 11 | 20 | 105 | (0.20, 0.27) |
| Example 12 | 30 | 112 | (0.21, 0.29) |

Comparative Example 13

An organic EL device in Comparative Example 13 is manufactured in the same manner as in Comparative Example 1 except for using Comparative Compound 1 in place of Compound 2 described in JP-A-2007-19462. The obtained EL device is subjected to application of DC constant voltage with a source measure unit Model 2400 (manufactured by Toyo Corporation) to emit light. It is confirmed that the emission of green light originating in Comparative Compound 1 is obtained.

Comparative Example 14

An organic EL device in Comparative Example 14 is manufactured in the same manner as in Comparative Example 13 except for changing the ratio of mCP and Comparative Compound 1 to 70/30. The obtained EL device is subjected to application of DC constant voltage with a source measure unit Model 2400 (manufactured by Toyo Corporation) to emit light. It is confirmed that the emission of green light originating in Comparative Compound 1 is obtained.

Example 13

An organic EL device in Example 13 is manufactured in the same manner as in Comparative Example 1 except for using Exemplified Compound 27 according to the invention in place of Compound 2 described in JP-A-2007-19462. The obtained EL device is subjected to application of DC constant voltage with a source measure unit Model 2400 (manufactured by Toyo Corporation) to emit light. It is confirmed that the emission of green light originating in Exemplified Compound 27 according to the invention is obtained.

Example 14

An organic EL device in Example 14 is manufactured in the same manner as in Example 13 except for changing the ratio of mCP and Exemplified Compound 27 according to the invention to 70/30. The obtained EL device is subjected to application of DC constant voltage with a source measure unit Model 2400 (manufactured by Toyo Corporation) to emit light. It is confirmed that the emission of green light originating in Exemplified Compound 27 according to the invention is obtained.

Relative luminance and CIE chromaticity of each of devices manufactured are shown in Table 7 below. From Table 7, it can be seen that the compound of the invention is little in chromaticity variation of light emission due to addition concentration even when the compound is added in high concentration.

TABLE 7

|  | Addition Concentration of Phosphorescent Material (%) | Relative Luminance at the Time of Application of 12 V | CIE Chromaticity |
|---|---|---|---|
| Comparative Example 13 | 20 | 100 | (0.31, 0.63) |
| Comparative Example 14 | 30 | 99 | (0.34, 0.57) |
| Example 13 | 20 | 103 | (0.31, 0.61) |
| Example 14 | 30 | 107 | (0.31, 0.59) |

Comparative Example 15

An organic EL device in Comparative Example 15 is manufactured in the same manner as in Comparative Example 1 except for using Comparative Compound 2 in place of Compound 2 described in JP-A-2007-19462. The obtained EL device is subjected to application of DC constant voltage with a source measure unit Model 2400 (manufactured by Toyo Corporation) to emit light. It is confirmed that the emission of green light originating in Comparative Compound 2 is obtained.

Comparative Example 16

An organic EL device in Comparative Example 16 is manufactured in the same manner as in Comparative Example 15 except for changing the ratio of mCP and Comparative Compound 2 to 70/30. The obtained EL device is subjected to application of DC constant voltage with a source measure unit Model 2400 (manufactured by Toyo Corporation) to emit light. It is confirmed that the emission of green light originating in Comparative Compound 2 is obtained.

Example 15

An organic EL device in Example 15 is manufactured in the same manner as in Comparative Example 1 except for using Exemplified Compound 30 according to the invention in place of Compound 2 described in JP-A-2007-19462. The obtained EL device is subjected to application of DC constant voltage with a source measure unit Model 2400 (manufactured by Toyo Corporation) to emit light. It is confirmed that the emission of green light originating in Exemplified Compound 30 according to the invention is obtained.

Example 16

An organic EL device in Example 16 is manufactured in the same manner as in Example 15 except for changing the ratio of mCP and Exemplified Compound 30 according to the invention to 70/30. The obtained EL device is subjected to application of DC constant voltage with a source measure unit Model 2400 (manufactured by Toyo Corporation) to emit light. It is confirmed that the emission of green light originating in Exemplified Compound 30 according to the invention is obtained.

Relative luminance and CIE chromaticity of each of devices manufactured are shown in Table 8 below. From Table 8, it can be seen that the compound of the invention is little in chromaticity variation of light emission due to addition concentration even when the compound is added in high concentration.

TABLE 8

|  | Addition Concentration of Phosphorescent Material (%) | Relative Luminance at the Time of Application of 12 V | CIE Chromaticity |
|---|---|---|---|
| Comparative Example 15 | 20 | 100 | (0.32, 0.56) |
| Comparative Example 16 | 30 | 107 | (0.33, 0.50) |
| Example 15 | 20 | 105 | (0.31, 0.55) |
| Example 16 | 30 | 111 | (0.30, 0.53) |

Example 17

An organic EL device in Example 17 is manufactured in the same manner as in Comparative Example 1 except for using Exemplified Compound 57 according to the invention in place of Compound 2 described in JP-A-2007-19462. The obtained EL device is subjected to application of DC constant voltage with a source measure unit Model 2400 (manufactured by Toyo Corporation) to emit light. It is confirmed that the emission of blue light originating in Exemplified Compound 57 according to the invention is obtained.

Example 18

An organic EL device in Example 18 is manufactured in the same manner as in Example 17 except for changing the ratio of mCP and Exemplified Compound 57 according to the invention to 70/30. The obtained EL device is subjected to application of DC constant voltage with a source measure unit Model 2400 (manufactured by Toyo Corporation) to emit light. It is confirmed that the emission of blue light originating in Exemplified Compound 57 according to the invention is obtained.

Relative luminance and CIE chromaticity of each of devices manufactured are shown in Table 9 below. From Table 9, it can be seen that the compound of the invention is little in chromaticity variation of light emission due to addition concentration even when the compound is added in high concentration.

TABLE 9

|  | Addition Concentration of Phosphorescent Material (%) | Relative Luminance at the Time of Application of 12 V | CIE Chromaticity |
|---|---|---|---|
| Comparative Example 1 | 20 | 100 | (0.19, 0.30) |
| Comparative Example 2 | 30 | 110 | (0.25, 0.33) |
| Example 17 | 20 | 100 | (0.18, 0.29) |
| Example 18 | 30 | 115 | (0.18, 0.31) |

By the use of other compounds according to the invention, also, chromaticity variation of light emission due to addition concentration of the phosphorescent material in the light-emitting layer is little, and organic electroluminescence devices capable of light emission in higher luminance can be manufactured by using the compounds according to the invention.

The invention can provide an organic electroluminescence device little in chromaticity change due to addition concentration of a phosphorescent material in a light-emitting layer and capable of emission in high luminance. The invention can further provide a metal complex compound suitable for the electroluminescence device.

The entire disclosure of each and every foreign patent application from which the benefit of foreign priority has been claimed in the present application is incorporated herein by reference, as if fully set forth.

What is claimed is:

1. A compound represented by the following formula (II):

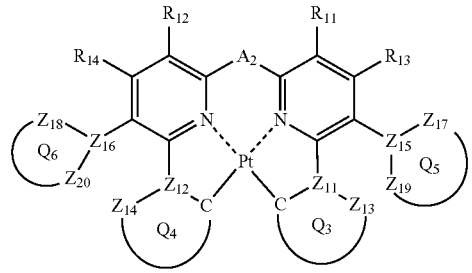

Formula (II)

wherein
each of ring $Q_5$ containing $Z_{15}$, $Z_{17}$ and $Z_{19}$, and ring $Q_6$ containing $Z_{16}$, $Z_{18}$ and $Z_{20}$, independently represents a 5- or 6-membered aromatic ring or aromatic heterocyclic ring;
each of $Z_{15}$, $Z_{16}$, $Z_{17}$, $Z_{18}$, $Z_{19}$ and $Z_{20}$, independently represents a carbon atom or a nitrogen atom;
each of a bond for bonding $Z_{15}$ to $Z_{17}$, a bond for bonding $Z_{15}$ to $Z_{19}$, a bond for bonding $Z_{16}$ to $Z_{18}$, and a bond for bonding $Z_{16}$ to $Z_{20}$ independently represents a single bond or a double bond, provided that when $Z_{15}$ represents a nitrogen atom, each of the bond for bonding $Z_{15}$ to $Z_{17}$ and the bond for bonding $Z_{15}$ to $Z_{19}$ represents a single bond, and when $Z_{16}$ represents a nitrogen atom, each of the bond for bonding $Z_{16}$ to $Z_{18}$ and the bond for bonding $Z_{16}$ to $Z_{20}$ represents a single bond;

$Z_{17}$, $Z_{18}$, $Z_{19}$ and $Z_{20}$ do not have a substituent;

each of ring $Q_3$ containing a carbon atom, $Z_{11}$ and $Z_{13}$, and ring $Q_4$ containing a carbon atom, $Z_{12}$ and $Z_{14}$, independently represents an aromatic ring or an aromatic heterocyclic ring;

each of $Z_{13}$ and $Z_{14}$ independently represents a carbon atom or a nitrogen atom;

each of $Z_{11}$ and $Z_{12}$ independently represents a carbon atom;

each of a bond for bonding $Z_{11}$ to the carbon atom coordinating to Pt contained in ring $Q_3$, a bond for bonding $Z_{11}$ to $Z_{13}$, a bond for bonding $Z_{12}$ to the carbon atom coordinating to Pt contained in ring $Q_4$, and a bond for bonding $Z_{12}$ to $Z_{14}$ independently represents a single bond or a double bond, $Z_{13}$ and $Z_{14}$ do not have a substituent;

each of $R_{11}$, $R_{12}$, $R_{13}$ and $R_{14}$ independently represents a hydrogen atom or a substituent; and $A_2$ represents a single bond or a divalent linking group.

2. The compound as claimed in claim 1, wherein the formula (II) is represented by the following formula (III):

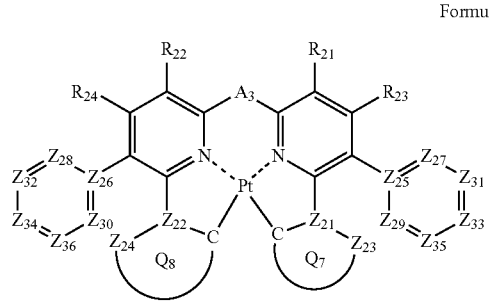

Formula (III)

wherein each of $Z_{25}$ and $Z_{26}$ represents a carbon atom;

each of $Z_{27}$, $Z_{28}$, $Z_{29}$, $Z_{30}$, $Z_{31}$, $Z_{32}$, $Z_{33}$, $Z_{34}$, $Z_{35}$ and $Z_{36}$ independently represents a carbon atom or a nitrogen atom;

$Z_{27}$, $Z_{28}$, $Z_{29}$ and $Z_{30}$ do not have a substituent;

each of $Z_{23}$ and $Z_{24}$ independently represents a carbon atom or a nitrogen atom;

each of $Z_{21}$ and $Z_{22}$ independently represents a carbon atom;

each of ring $Q_7$ containing a carbon atom, $Z_{21}$ and $Z_{23}$, and ring $Q_8$ containing a carbon atom, $Z_{22}$ and $Z_{24}$ independently represents an aromatic ring or an aromatic heterocyclic ring;

each of a bond for bonding $Z_{21}$ to the carbon atom coordinating to Pt contained in ring $Q_7$, a bond for bonding $Z_{21}$ to $Z_{23}$, a bond for bonding $Z_{22}$ to the carbon atom coordinating to Pt contained in ring $Q_8$, and a bond for bonding $Z_{22}$ to $Z_{24}$ independently represents a single bond or a double bond;

$Z_{23}$ and $Z_{24}$ do not have a substituent;

each of $R_{21}$, $R_{22}$, $R_{23}$ and $R_{24}$ independently represents a hydrogen atom or a substituent; and $A_3$ represents a single bond or a divalent linking group.

3. The compound as claimed in claim 2, wherein the formula (III) is represented by the following formula (IV):

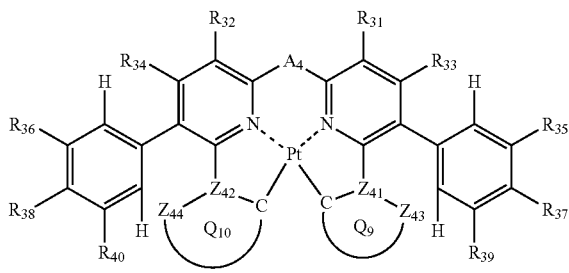

Formula (IV)

wherein each of $Z_{43}$ and $Z_{44}$ independently represents a carbon atom or a nitrogen atom;

each of $Z_{41}$ and $Z_{42}$ independently represents a carbon atom;

each of ring $Q_9$ containing a carbon atom, $Z_{41}$ and $Z_{43}$, and ring $Q_{10}$ containing a carbon atom, $Z_{42}$ and $Z_{44}$, independently represents an aromatic ring or an aromatic heterocyclic ring;

each of a bond for bonding $Z_{41}$ to the carbon atom coordinating to Pt contained in ring $Q_9$, a bond for bonding $Z_{41}$ to $Z_{43}$, a bond for bonding $Z_{42}$ to the carbon atom coordinating to Pt contained in ring $Q_{10}$, and a bond for bonding $Z_{42}$ to $Z_{44}$ independently represents a single bond or a double bond;

$Z_{43}$ and $Z_{44}$ do not have a substituent;

each of $R_{31}$, $R_{32}$, $R_{33}$, $R_{34}$, $R_{35}$, $R_{36}$, $R_{37}$, $R_{38}$, $R_{39}$ and $R_{40}$ independently represents a hydrogen atom or a substituent; and $A_4$ represents a single bond or a divalent linking group.

4. The compound as claimed in claim 3, wherein the formula (IV) is represented by the following formula (V):

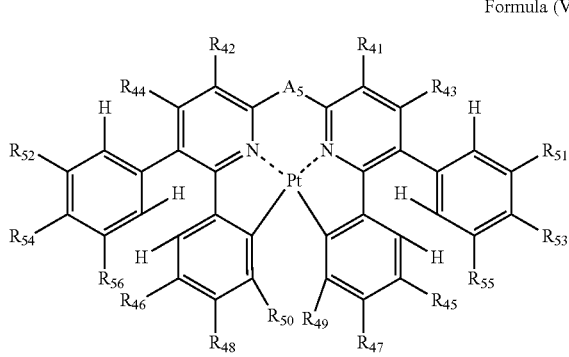

Formula (V)

wherein each of $R_{41}$, $R_{42}$, $R_{43}$, $R_{44}$, $R_{45}$, $R_{46}$, $R_{47}$, $R_{48}$, $R_{49}$, $R_{50}$, $R_{51}$, $R_{52}$, $R_{53}$, $R_{54}$, $R_{55}$ and $R_{56}$ independently represents a hydrogen atom or a substituent; and $A_5$ represents a single bond or a divalent linking group.

5. The compound as claimed in claim 1, wherein the formula (II) is represented by the following formula (VII):

Formula (VII)

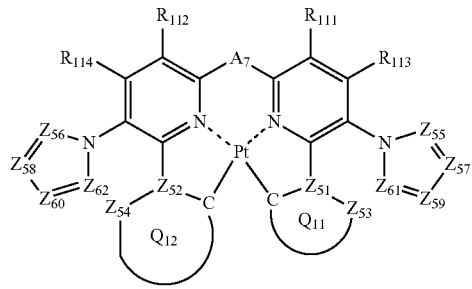

wherein each of $Z_{55}$, $Z_{56}$, $Z_{57}$, $Z_{58}$, $Z_{59}$, $Z_{60}$, $Z_{61}$ and $Z_{62}$ independently represents a carbon atom or a nitrogen atom;

$Z_{55}$, $Z_{56}$, $Z_{61}$ and $Z_{62}$ do not have a substituent;

each of $Z_{53}$ and $Z_{54}$ independently represents a carbon atom or a nitrogen atom;

each of $Z_{51}$ and $Z_{52}$ independently represents a carbon atom each of ring $Q_{11}$ containing a carbon atom, $Z_{51}$ and $Z_{53}$, and ring $Q_{12}$ containing a carbon atom, $Z_{52}$ and $Z_{54}$, independently represents an aromatic ring or an aromatic heterocyclic ring;

each of a bond for bonding $Z_{51}$ to the carbon atom coordinating to Pt contained in ring $Q_{11}$, a bond for bonding $Z_{51}$ to $Z_{53}$, a bond for bonding $Z_{52}$ to the carbon atom coordinating to Pt contained in ring $Q_{12}$, and a bond for bonding $Z_{52}$ to $Z_{54}$ independently represents a single bond or a double bond;

$Z_{53}$ and $Z_{54}$ do not have a substituent;

each of $R_{111}$, $R_{112}$, $R_{113}$ and $R_{114}$ independently represents a hydrogen atom or a substituent; and $A_7$ represents a single bond or a divalent linking group.

6. The compound as claimed in claim 5, wherein the formula (VII) is represented by the following formula (VIII):

Formula (VIII)

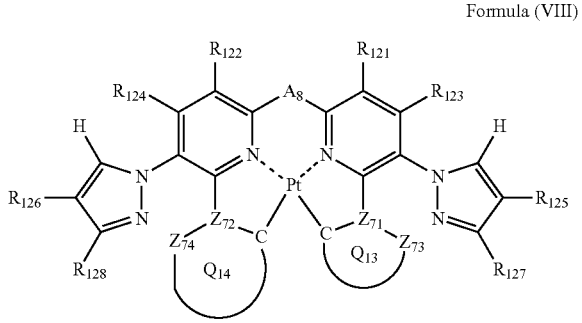

wherein each of $Z_{73}$ and $Z_{74}$ independently represents a carbon atom or a nitrogen atom;

each of $Z_{71}$ and $Z_{72}$ independently represents a carbon atom;

each of ring $Q_{13}$ containing a carbon atom, $Z_{71}$ and $Z_{73}$, and ring $Q_{14}$ containing a carbon atom, $Z_{72}$ and $Z_{74}$, independently represents an aromatic ring or an aromatic heterocyclic ring;

each of a bond for bonding $Z_{71}$ to the carbon atom coordinating to Pt contained in ring $Q_{13}$, a bond for bonding $Z_{71}$ to $Z_{73}$, a bond for bonding $Z_{72}$ to the carbon atom coordinating to Pt contained in ring $Q_{14}$, and a bond for bonding $Z_{72}$ to $Z_{74}$ independently represents a single bond or a double bond;

$Z_{73}$ and $Z_{74}$ do not have a substituent;

each of $R_{121}$, $R_{122}$, $R_{123}$, $R_{124}$, $R_{125}$, $R_{126}$, $R_{127}$ and $R_{128}$ independently represents a hydrogen atom or a substituent; and $A_8$ represents a single bond or a divalent linking group.

7. The compound as claimed in claim 6, wherein the formula (VIII) is represented by the following formula (IX):

Formula (IX)

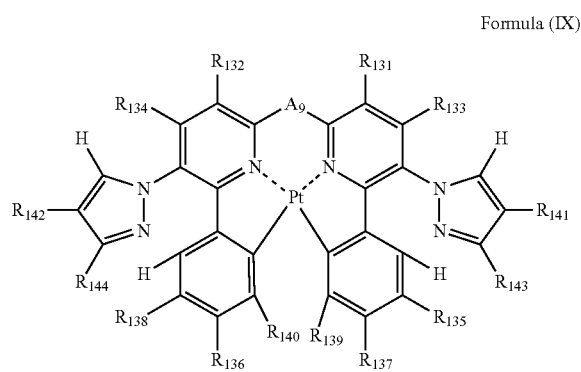

wherein each of $R_{131}$, $R_{132}$, $R_{133}$, $R_{134}$, $R_{135}$, $R_{136}$, $R_{137}$, $R_{138}$, $R_{139}$, $R_{140}$, $R_{141}$, $R_{142}$, $R_{143}$ and $R_{144}$ independently represents a hydrogen atom or a substituent; and $A_9$ represents a single bond or a divalent linking group.

8. An organic electroluminescence device comprising:
a pair of electrodes; and
an organic layer between the pair of electrodes,
wherein the organic layer contains the compound as claimed in claim 1.

9. The organic electroluminescence device of claim 8, wherein the organic layer is a light-emitting layer.

10. The organic electroluminescence device of claim 9, wherein the light- emitting layer further comprises a host material.

11. The organic electroluminescence device of claim 8, wherein the organic layer is formed by a dry film-forming method.

12. An organic electroluminescence device comprising:
a pair of electrodes, and
a light-emitting layer between the pair of electrodes,
wherein the light-emitting layer contains the compound as claimed in claim 1 in a proportion of from 20 to 30 wt % of the total mass of the light-emitting layer.

13. The organic electroluminescence device of claim 12, wherein the light- emitting layer further comprises a host material.

* * * * *